(12) United States Patent
Mueller

(10) Patent No.: US 10,758,430 B1
(45) Date of Patent: Sep. 1, 2020

(54) STAY WET POTTY TRAINING LINER

(71) Applicant: Quixotic Innovations, LLC, Austin, TX (US)

(72) Inventor: Lori Mueller, Austin, TX (US)

(73) Assignee: Quixotic Innovations, LLC, Austin, TX (US)

( * ) Notice: Subject to any disclaimer, the term of this patent is extended or adjusted under 35 U.S.C. 154(b) by 242 days.

(21) Appl. No.: 15/864,601

(22) Filed: Jan. 8, 2018

(51) Int. Cl.
| G09B 19/00 | (2006.01) |
| A61F 13/513 | (2006.01) |
| A61F 13/56 | (2006.01) |
| A61F 13/47 | (2006.01) |

(52) U.S. Cl.
CPC ........ *A61F 13/51305* (2013.01); *A61F 13/47* (2013.01); *A61F 13/5611* (2013.01); *G09B 19/0076* (2013.01); *A61F 2013/4708* (2013.01)

(58) Field of Classification Search
USPC ......... 434/247; 604/327, 367–369, 378–382, 604/385.01, 385.03, 386, 387
See application file for complete search history.

(56) References Cited

U.S. PATENT DOCUMENTS

| 4,413,996 A * | 11/1983 | Taylor ............... A61F 13/49473 604/382 |
| 4,994,052 A * | 2/1991 | Kimura ................ A61F 5/4401 604/358 |
| 5,807,367 A * | 9/1998 | Dilnik .................. A61F 13/494 604/369 |
| 5,895,382 A * | 4/1999 | Popp ................ A61F 13/49014 604/385.21 |
| 6,133,501 A * | 10/2000 | Hallock ................ A61F 13/495 604/369 |
| 6,346,097 B1 * | 2/2002 | Blaney .................. A61F 13/495 604/327 |
| 7,037,298 B2 * | 5/2006 | Ohshima ............. A61F 13/4752 604/385.01 |
| 7,160,280 B2 * | 1/2007 | Bailey .................. A61F 13/495 604/348 |
| 7,252,657 B2 * | 8/2007 | Mishima ............... A61F 13/494 604/385.24 |
| 7,666,173 B2 * | 2/2010 | Mishima ............. A61F 13/4915 604/385.101 |
| 7,749,208 B2 * | 7/2010 | Moberg-Alehammar ................... A61F 13/505 604/369 |
| 7,812,213 B2 * | 10/2010 | Doverbo ........... A61F 13/15699 604/358 |
| D678,517 S * | 3/2013 | Periman ...................... D24/124 |
| 9,173,786 B2 * | 11/2015 | Roh .................... A61F 13/5616 |
| 9,456,935 B2 * | 10/2016 | Greening, II ..... A61F 13/49473 |
| 2010/0312216 A1 * | 12/2010 | Periman ............. A61F 13/4755 604/385.04 |
| 2013/0281949 A1 * | 10/2013 | Periman ................. A61L 15/20 604/361 |

* cited by examiner

*Primary Examiner* — Kurt Fernstrom
(74) *Attorney, Agent, or Firm* — Lee & Hayes, P.C.

(57) ABSTRACT

A potty training liner configured to fit within an undergarment of a child. The potty training liner includes a first and second channel wall that form a channel to allow fluid to move front to back within the channel after an accident. The potty training liner may also have reduced absorption levels to aid in encouraging a child to become potty trained.

20 Claims, 12 Drawing Sheets

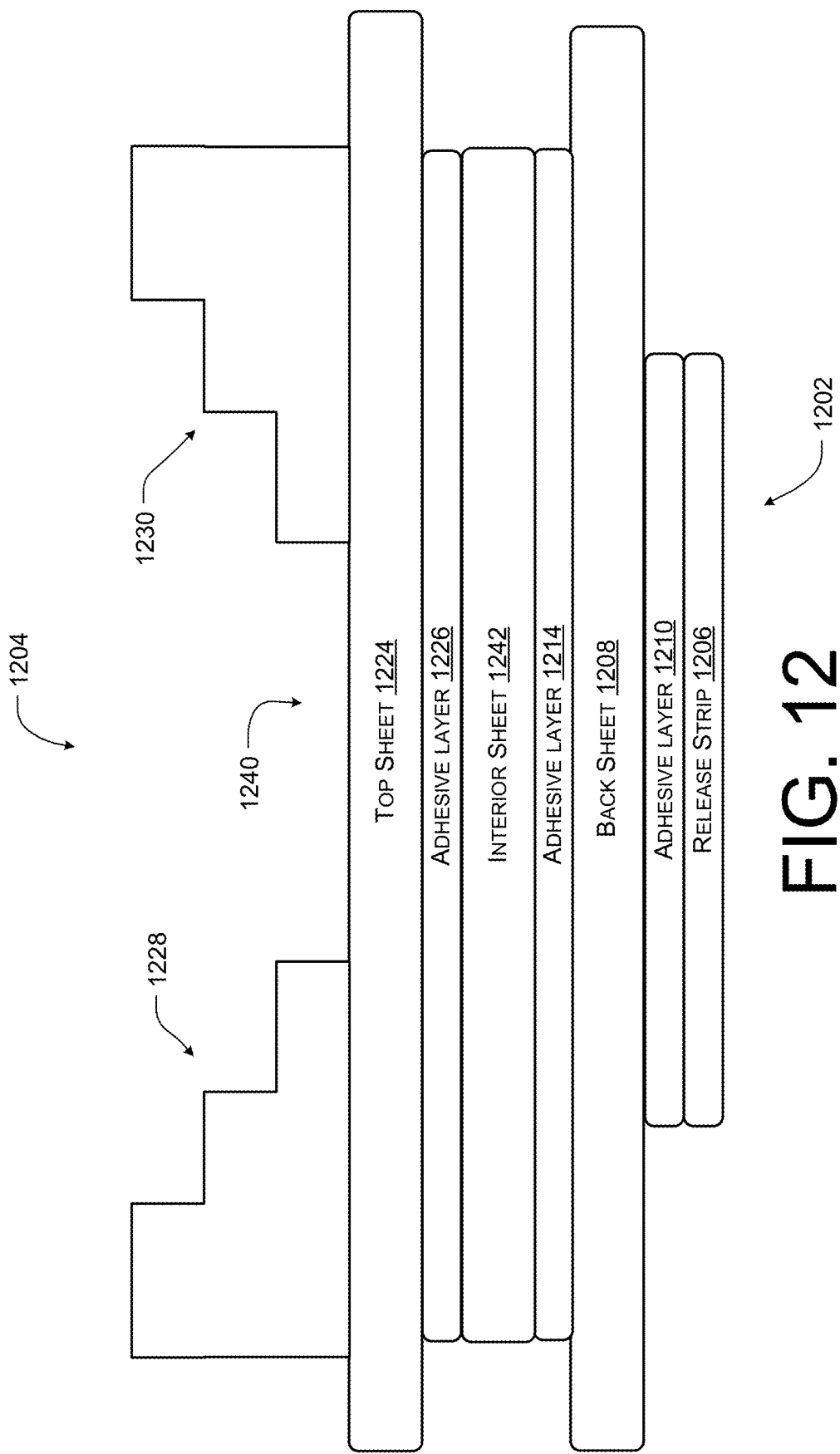

STAY WET POTTY TRAINING LINER

BACKGROUND

It is common today for parents to delay potty training of children. For instance, prior to the advent of disposable diapers and training pants, the average age for potty training children was between 18 and 24 months. With the advent and improvements of disposable diapers and training garments (such as pull-ups), the average age of potty training children has crept up to between 3 and 4 years. As a result, the industry has produced larger diapers and potty training garments with greater absorption capacity, improved wicking of fluids, and faster absorption. However, increases and improvements in absorption amount and rate of both diapers and potty training garments, such as pull-ups, actually reduce the desire and effectiveness of the potty training, as the child remains comfortable and dry. Thus, the overall increase in the average age of potty training.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

FIG. 12 illustrates another example cross sectional view of a potty training liner according to some implementations.

DETAILED DESCRIPTION

Figure 1:
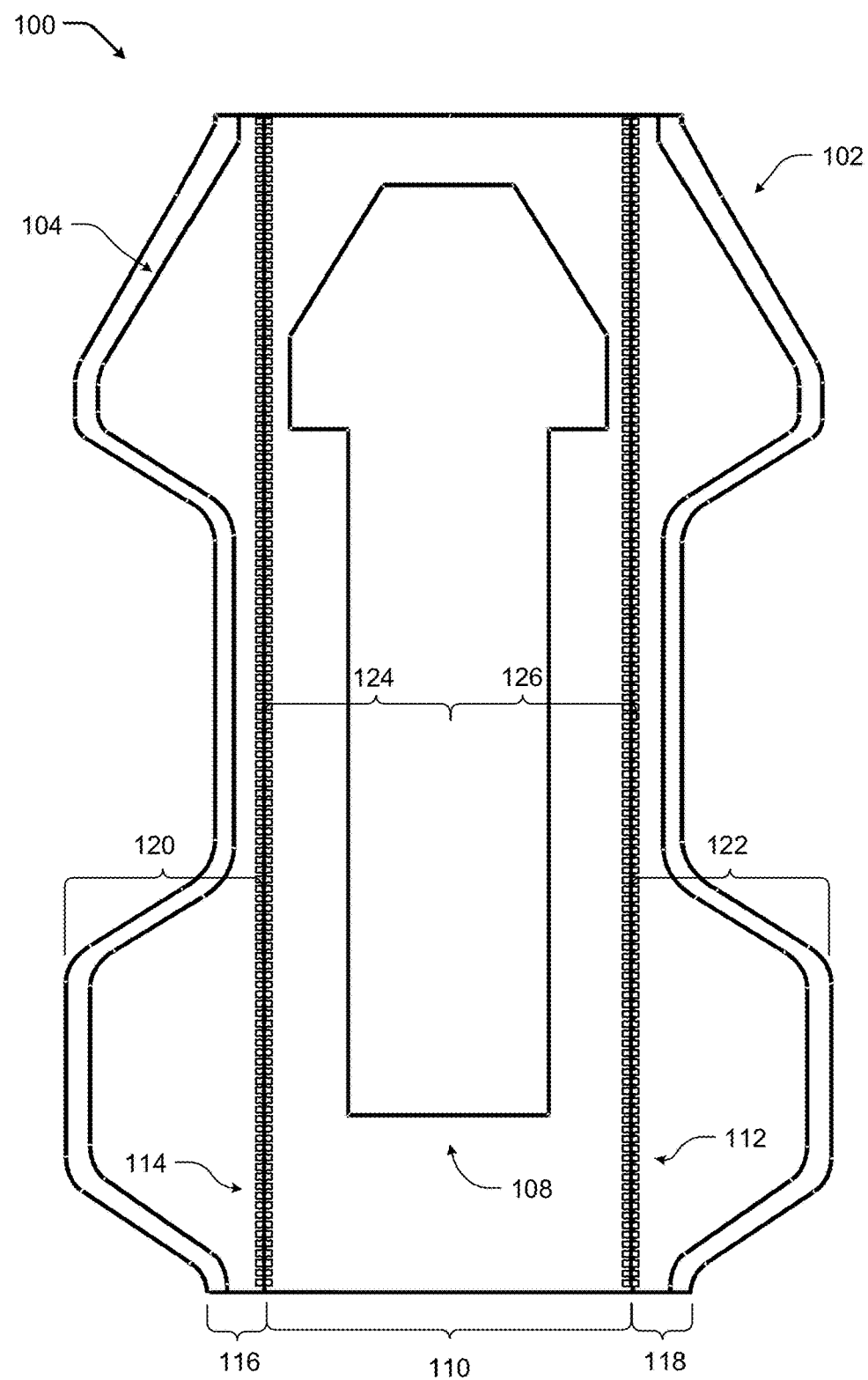
FIG. 1 illustrates an example top view of the potty training liner according to some implementations.

Described herein are potty training liners designed to fit between the skin of the user (e.g., the child undergoing potty training) and undergarments (such as underwear). Thus, the potty training liners are in direct contact with the skin of the child and held in place solely by pressure applied by the undergarment. Most children do not want to soil their clothes and are often embarrassed at their mistakes. A child who has some bladder control knows he "has to go," but simply waits too long, or gets distracted and forgets he has to go. This typically results in a child not quite making it to the bathroom in time. The potty training liner can provide sort term emergency protection in this situation and prevent a child from soiling their clothes, and other items. However, unlike conventional potty training garments, the potty training liner discussed herein, creates awareness of the accident by providing reduced absorption, slowing the rate of absorption, and causing the fluids to move against the child's skin within the liner. Thus, the potty training liners discussed herein, are designed for preferable use as "short-term" emergency protection, whereas diapers, potty training garments (such as "pull ups"), and sanitary pads are designed for "long-term" wearable protection.

For instance, in some implementations, the potty training liners may include a partial hydrophobic top sheet over an interior section. The interior section may be positioned atop a polyethylene nonwoven hydrophobic back sheet. In some specific examples, an adhesive layer may be associated with the hydrophobic back sheet on a side opposite the interior section. The adhesive may be configured to releasably adhere to a child's undergarments to hold the potty training liner in place during use.

Thus, unlike, potty training garments (such as pull-ups) that have properties that make them similar to diapers, the liner described herein operates in a manner that is different and, thus, noticeable by the child undergoing training. For example, training garments are often pull-on or all-in-one solutions that are applied by the adult to the child such that the child does not realize and understand the difference between the diaper and the training garment. Additionally, conventional potty training garments are highly absorbent and wick fluid away from the body quickly and efficiently. The conventional training garments are not as breathable as cloth underwear and often keep the child feeling comfortable and dry after an accident in such an effective manner that the child often does not know that the child has had an incident. Thus, the negative training incentives (e.g., wetness, embarrassment, etc.) are less effective. In some cases, such as when the child is unaware of the incident, the training opportunity is missed (e.g., the adult or parent is unable to confront and discuss the situation with the child), thereby reducing the effectiveness of the training.

The potty training liner, discussed herein, is also unlike conventional potty training garments, as the liner is thin (e.g., less than 5.0 mm thick), while the conventional potty training garment is typically greater than 10 mm thick. In some implementations, the dry thickness of the potty training liner may be less than 5.0 mm, less than 4.0 mm, less than 2.0 mm, or less than 0.7 mm thick. In some cases, the potty training liner may be between 276 mm long and 245 mm long. In other examples, the potty training liner may be less than 0.5 mm thick. The potty training liner may also have a folded thickness of less than 7.0 mm, less than 5.0 mm, less than 3.0 mm, or less than 1.0 mm while conventional potty training garments typically have a folded thickness of greater than 20 mm. Thus, the potty training liner, discussed herein, are unlike conventional potty training garments which have a bulky "diaper like" feel to them and are too similar to the traditional diapers a child has worn since birth. Accordingly, the use of conventional potty training garments for potty training can send confusing messages to children further delaying completion of potty training.

In one example, the potty training liner may be less than 6 millimeter (mm), 5 mm, 4 mm, 2 mm or 0.75 mm thick, excluding the channel wall height, less than 248 mm long (from front to back) and less than 120 mm wide (at the largest point) and less than 63.5 mm wide (at the narrowest point). In some cases, the potty training liner may be less than 180 grammage (gsm) in capacity or less than 190 gsm.

The potty training liner may also have a roughly arrow like shape that includes a first wide region (e.g., a back region), a narrow region (e.g., the leg region), and a second wide region (e.g., the front region).

In some cases, the first wide region may generally have the shape of the first the arrow fletching (e.g., the feathers). In some implementations, the fletching shape may include corners, while in other cases, the fletching shape may include curved corners to improve the ease of manufacturing. In some cases, the length of the first wide region may be 85.76 mm. In some examples, the length of the first wide region may be between 80 mm and 100 mm or between 85 mm and 90 mm.

The first wide region may, in some implementations, vary from 101.6 mm to 63.5 mm wide. In another example, the first wide region may have a maximum width of between 90 mm and 105 mm and a minimum width of between 55 mm and 70 mm. In some cases, the first wide region may have a minimum width of 80 mm or 70 mm. In one example, the profile of the potty training liner may gradually slope inward from the first wide region may (the maximum width) to the width of the narrow leg region (the minimum width).

In some cases, the narrow leg region may vary from 62 mm wide to 64 mm wide. In some specific examples, the narrow leg region may be 63.5 mm wide. In the implementations in which curved corners are utilized, the radius of the corners may be approximately 12.7° or a range from 12° to 13°. In some implementations, the width of the first wide region may be expressed as a ratio with respect to the narrow leg region. For example, the first wide region may be 1.6 or 1.5 times the width of the narrow leg region at the widest point. The narrow leg region may have a length of 76.17 mm or approximately 76 mm. In some examples, the length of the narrow leg region may be between 75 mm and 80 mm, between 70 mm and 85 mm, or between 70 mm and 85 mm.

In some cases, the second wide region may generally have the shape of an arrowhead. In another implementation, the second wide region may vary from 101.6 mm to 63.5 mm wide. For instance, the tip of the arrowhead shape may be 63.5 mm wide and the base of the arrowhead shape may be 101.6 mm wide. In other cases, the tip of the arrowhead may be between 60 mm and 65 mm wide and the base of the arrowhead may be between 100 mm and 105 mm. In some implementations, the width of the second wide region may be expressed as a ratio with respect to the narrow leg region. In some cases, the length of the second wide region may be 85.73 mm or approximately 85 mm. In some examples, the length of the narrow leg region may be between 80 mm and 90 mm, between 85 mm and 90 mm, or between 75 mm and 95 mm.

In some implementations, the potty training liner may include a channel wall that extends the full length of the potty training liner from a front side to a back side. For example, the liner may be 247.66 mm long and the channel wall may also be 247.66 mm long. In other words, the channel wall extends the entire length of the liner from front to back at a full height or above a particular minimum height. The channel wall may be formed from an elastic yarn and a hydrophobic polyethylene material. The channel wall may be designed to cause fluid within the potty training liner to channel from the front of the liner to the back of the liner and vice versa. Thus, the channel wall may extend upwards from the base or top sheet of the potty training liner for the entire length of the liner, applied to the top sheet or extend upward from the top sheet.

In some cases, the channel wall may be greater than 1.0 inches tall. In other cases, the channel wall may be greater than 1.5 inches tall. In a specific case, the channel wall may be greater than or equal to 2.0 inches tall. In some instances, the channel wall may vary from half an inch to one inch tall, such that the channel wall is shorter near the front end and the back end than in the middle of the potty training liner. In one example, the channel wall may be less than 0.5 mm, 1 mm, 2 mm, or 4 mm wide. In another instance, the channel wall may be less than 4 mm wide. In still other instances, the channel wall may be less than 5 mm wide or less than 6 mm wide.

The channel wall may also be configured to maintain a predetermined distance from the edge (e.g., both the left and right side of the potty training liner). For example, the channel wall may be greater than 29 mm from the edge of the potty training liner at the maximum width and greater than 10 mm from the edge of the potty training liner at the narrowest width. Thus, the channel wall may be greater than 10 mm form the edge of the potty training liner for the full length of the liner. In another example, the channel wall may be a at least 5 mm from the edge of the potty training liner for the full length of the liner. In another example, the channel wall may be greater than 12 mm from the edge of the potty training liner or greater than 15 mm from the edge of the potty training liner. In this example, the placement of the channel wall at the predetermined distance from the edge of the potty training liner and the height of the channel walls allows the potty training liner, discussed herein, to form a channel that allows fluid to move forward and backwards within the channel (e.g., the space between the channel walls), such that during use the child feels an uncomfortable sensation of moving fluid against the child's skin following an insult or accident. Thus, the potty training liner discussed herein is unlike and operates in a manner different form the conventional barrier leg cuff that is proximate or adjacent to the edge of the liner and used to prevent leakage at the time of insult.

The channel wall may also be configured to maintain a predetermined distance from the interior or center line of the potty training liner. For example, the channel wall may be approximately 17.43 mm from the center line of the potty training liner on each side. In other implementations, the channel wall may be approximately 15 mm, 10 mm, or 8 mm from the center line of the potty training liner on each side. In some cases, the channel wall may be between 17 mm and 18 mm from the center line of the potty training liner. In another example, the channel walls may be approximately 20-25 mm from the center line.

In some implementations, the interior section may also be configured in the generally arrow shape having a first wide region (back region), a narrow leg region, and a second wide region (front region). The interior section may have a relative small thickness when dry. For example, the dry thickness of the interior section may be less than 8.0 mm thick, less than 5.0 mm thick, less than 1.0 mm thick, or less than 0.7 mm thick. One specific example, the interior section may be between 0.09 mm and 0.12 mm thick when dry.

In some cases, the first wide region of the interior section may generally have the shape of the first the arrow fletching (e.g., the feathers). In some implementations, the fletching shape may include corners, while in other cases, the fletching shape may include curved corners to improve the ease of manufacturing. In some cases, the length of the first wide region of the interior section may be 89.6 mm or 90 mm. In some examples, the length of the first wide region of the interior section may be between 80 mm and 110 mm or between 85 mm and 100 mm.

The first wide region of the interior section may, in some implementations, vary from 101.6 mm to 63.5 mm wide. In another example, the first wide region of the interior section may have a maximum width of between 90 mm and 105 mm and a minimum width of between 55 mm and 70 mm. In one example, the first wide region of the interior section may gradually slope inward from the maximum width to the width of the narrow leg region of the interior section.

In some cases, the narrow leg region of the interior section may vary from 62 mm wide to 64 mm wide. In some specific examples, the narrow leg region of the interior section may be 63.5 mm wide. In the implementations in which curved corners are utilized, the radius of the corners may be approximately 12.7° or a range from 12° to 13°. In some implementations, the width of the first wide region may be expressed as a ratio with respect to the narrow leg region. For example, the first wide region of the interior section may be 1.6 or 1.5 times the width of the narrow leg region of the interior section at the widest point. The narrow leg region of the interior section may have a length of 76.17 mm or approximately 76 mm. In some examples, the length of the narrow leg region of the interior section may be between 75 mm and 80 mm, between 70 mm and 85 mm, or between 70 mm and 85 mm.

In some cases, the second wide region of the interior section may generally have the shape of an arrowhead. In another implementation, the second wide region of the interior section may vary from 101.6 mm to 63.5 mm wide. For instance, the tip of the arrowhead shape may be 63.5 mm wide and the base of the arrowhead shape may be 101.6 mm wide. In other cases, the tip of the arrowhead may be between 60 mm and 65 mm wide and the base of the arrowhead may be between 100 mm and 105 mm. In some implementations, the width of the second wide region of the interior section may be expressed as a ratio with respect to the narrow leg region of the interior section. In some cases, the length of the second wide region of the interior section may be 85.73 mm or approximately 85 mm. In some examples, the length of the narrow leg region may be between 80 mm and 90 mm, between 85 mm and 90 mm, or between 75 mm and 95 mm.

In some cases, the length of the interior section may also have a length that is less than the length of the back sheet and topsheet of the liner (e.g., the interior section does not extend from the front to the back of the potty training liner). For example, as discussed above, the potty training liner may be approximately 275.35 mm long and the interior section may be approximately 201.35 mm long. In another example, the interior section may be approximately 216.71 mm long. In still another example, the interior section may be 241.48 mm long. In some cases, the interior section may vary between 200 mm long and 270 mm long, for instance, 245 mm long.

In some implementations, the width of the second wide region of the interior section may be expressed as a ratio with respect to the narrow region of the interior section. For example, the second wide region of the interior section may be 3 times the width of the narrow region of the interior section at the widest point. In another example, the ratio may be approximately 4 to 1. In some cases, the ratio may be greater than 3:1 or greater than 4:1. Additionally, the first wide region of the interior section may be expressed as a ratio of the second wide region of the interior section. In this example, the first wide region of the interior section may be 1.2 times the width of the second wide region of the interior section at the narrowest point of both. In other example, the first wide region of the interior section may be 2 times the width of the second wide region of the interior section at the narrowest point of both. Likewise, the second wide region of the interior section may be 1.1 or 1.2 times the width of the first wide region of the interior section. In other example, the first wide region of the interior section may be 1 times the width of the second wide region of the interior section at the widest point of both.

In the present examples, the interior section may be configured to be a first predetermined distance from a front end of the potty training liner (e.g., the end to fit in front a child using the liner) and a second predetermined distance form the back end of the potty training liner (e.g., the end to fit behind a child using the liner). In some examples, the first predetermined distance may be 25.71 mm, 25.76 mm, or a value between 25 and 26 mm from the front of the potty training liner. In some cases, the first predetermined distance may be between 20 mm and 30 mm from the front of the potty training liner. In some examples, the second predetermined distance may be 48.24 mm, 32.88 mm, or a value between 32 and 49 mm from the back of the potty training liner. In some cases, the second predetermined distance may be between 30 mm and 50 mm from the back of the potty training liner. In some specific examples, the predetermined distance may be less than 18 mm or less than 7 mm from the front or back of the liner. In one implementation, the interior section may be 17.03 mm from the front of the liner and 7 mm from the back of the liner.

Similarly, the interior section may maintain a third predetermined distance from the first side of the potty training liner (e.g., the side perpendicular to the front and back of the potty training liner) and a fourth predetermined distance form the second side of the potty training liner (e.g., the side opposite the first side). In some case, the third predetermined distance and the second predetermined distance may be the same. For example, at the point at which the interior section is nearest the edge of the liner the third predetermined distance and the fourth predetermined distance may be 3.17 mm. In some case, at the point at which the interior section is nearest the edge of the liner the third predetermined distance and the fourth predetermined distance may be between 2 mm and 5 mm or between 2 mm and 10 mm. Likewise, at the point at which the interior section is farthest from the edge of the liner the third predetermined distance and the fourth predetermined distance may be 3.27 mm. In some case, at the point at which the interior section is nearest the edge of the liner the third predetermined distance and the fourth predetermined distance may be between 2 mm and 5 mm or between 2 mm and 10 mm.

In some implementations, the interior section may be configured to absorb some of the fluids associated with an insult or accident. For example, the interior section may be configured to collect urine more centrally, increasing awareness. As the interior section becomes saturated, the liner begins to feels awkward and heavy between the child's legs, prompting the child to take action. In some examples, the interior section may be configured to increase or swell greatly in size in response to absorbing liquid. For example, the interior section may swell or cause the liner to swell to 1,000 times the original dry thickness. In another example, the interior section may swell to 500 times the original dry thickness. In some cases, the interior section may be configured to absorb less than an average insult of a child which may be as low as 40 milliliters (ml) or liquid (e.g., urine). Thus, the potty training liner may become fully saturated following a single insult or accident.

In some implementations, the interior section may be configured to absorb less than a predetermined amount of liquid or at a rate below a predefined rate. For example, the interior section may absorb less than 40 ml of liquid, less than 80 ml of liquid, less than 100 ml of liquid, or less than 200 ml of liquid. In some cases, the interior section may absorb between 40 ml and 60 ml, between 50 ml and 60 ml, between 40 ml and 80 ml. In some cases, the interior section may be configured to absorb liquid (such as urine) at a rate of less than 2 ml/min, 5 ml/min, less than 10 ml/minute, or less than 20 ml/min.

In some cases, the potty training liner in whole, rather than simply the interior section may be configured to absorb less than 40 ml of liquid, less than 80 ml of liquid, less than 100 ml of liquid, or less than 200 ml of liquid. In some cases, the potty training liner may absorb between 40 ml and 60 ml, between 50 ml and 60 ml, between 40 ml and 80 ml. In some cases, the potty training liner may be configured to absorb liquid (such as urine) at a rate of less than 2 ml/min, 5 ml/min, less than 10 ml/minute, or less than 20 ml/min.

In some implementations, the interior section may include an acquisition distribution layer (ADL) disposed over an interior section. In this implementation, the interior section may be disposed over a super absorbent polymer (SAP) layer. In some cases, the interior section may be some combination of pulp fluff, fiber, and/or absorbent or super absorbent material. In another implementation, the interior section may the SAP layer may be disposed over the interior section. In conventional potty training garments, the placement of the SAP layer over the interior section is undesirable, as the SAP layer can form a gel block as the SAP swells and prevent the fluid from reaching the interior section and being absorbed. However, in the potty training liner discussed herein, the SAP layer may function to limit or slow the amount of fluid absorbed by the interior section via gel blocking, resulting in the child becoming aware or discomforted by the unabsorbed fluid.

In another implementation, the interior section may include an ADL and a SAP layer but not an interior section. In this example, the ADL may be disposed over the SAP layer. In yet another implementation, the interior section may include only a SAP layer adhered between the top sheet and the back sheet. In still another example, the interior section may include only a ADL. In these implementation, the overall dry thickness of the potty training liner may be greatly reduced. For example, the dry thickness may be less than 4.0 mm, less than 3.0 mm, less than 2.0 mm, or less than 1.0 mm. In one additional implementation, the interior section may include the ADL with an integrated top sheet, such that the top sheet and the interior section are combined into a single layer. In this example, the potty training liner may include the top sheet adhered to the back sheet (or the interior section adhered to the back sheet). In some cases, the interior section may also be formed with a sponge with or without the addition of an interior section.

In some examples, the top sheet may be approximately 16 gsm and have a dry thickness of approximately 0.112 mm or less than 0.25 mm. Likewise, the back sheet may be approximately 0.07 mm thick (or less than 0.25 mm) when dry and approximately 9 gsm in capacity. The top sheet and back sheet may have width and length dimensions that are substantially similar to the overall potty training liner. For example, the top sheet and back sheet may also have the substantially arrow shape with a first wide region, a narrow region, and a second wide region. In some cases, the first wide region of the top sheet or back sheet may be 85.76 mm long. In some examples, the length of the first wide region of the top sheet or back sheet may be between 80 mm and 100 mm or between 85 mm and 90 mm. The first wide region of the top sheet or back sheet may, in some implementations, vary from 101.6 mm to 63.5 mm wide. In another example, the first wide region of the top sheet or back sheet may have a maximum width of between 90 mm and 105 mm and a minimum width of between 55 mm and 70 mm. In one example, the first wide region of the top sheet or back sheet may gradually slope inward from the maximum width to the width of the narrow leg region.

In some cases, the narrow leg region of the top sheet or back sheet may vary from 62 mm wide to 64 mm wide. In some specific examples, the narrow leg region may be 63.5 mm wide. In the implementations in which curved corners are utilized, the radius of the corners may be approximately 12.7° or a range from 12° to 13°. In some implementations, the width of the first wide region of the top sheet or back sheet may be expressed as a ratio with respect to the narrow leg region of the top sheet or back sheet. For example, the first wide region may be 1.6 or 1.5 times the width of the narrow leg region at the widest point. The narrow leg region may have a length of 76.17 mm or approximately 76 mm. In some examples, the length of the narrow leg region may be between 75 mm and 80 mm, between 70 mm and 85 mm, or between 70 mm and 85 mm.

In some cases, the second wide region of the top sheet or back sheet may generally have the shape of an arrowhead. In another implementation, the second wide region of the top sheet or back sheet may vary from 101.6 mm to 63.5 mm wide. For instance, the tip of the arrowhead shape may be 63.5 mm wide and the base of the arrowhead shape may be 101.6 mm wide. In other cases, the tip of the arrowhead may be between 60 mm and 65 mm wide and the base of the arrowhead may be between 100 mm and 105 mm. In some implementations, the width of the second wide region of the top sheet or back sheet may be expressed as a ratio with respect to the narrow leg region. In some cases, the length of the second wide region of the top sheet or back sheet may be 85.73 mm or approximately 85 mm. In some examples, the length of the narrow leg region may be between 80 mm and 90 mm, between 85 mm and 90 mm, or between 75 mm and 95 mm.

In some implementations, the top sheet and interior section may also include a concave depression or hydrophobic area, to cause fluid to pool centrally, or alternatively move fluid laterally to outer areas of the absorbent interior section. For example, the first wide region of the concave depression in the top sheet may, in some implementations, vary from 52.03 mm to 12.7 mm wide. In another example, the first wide region of the concave depression may vary from 57.16 mm to 19.06 mm wide. In still other examples, the first wide region of the concave depression may vary from 55 mm to 12 mm wide. For example, the narrow region may be 12 mm wide and, thus, the first wide region of the interior section may gradually slope inward from the maximum width of approximately 55 mm to the width of the narrow region of the core. In some cases, the narrow leg region of the concave depression may vary from 6 mm wide to 12 mm wide. In some specific examples, the narrow region of the concave depression may be 6.35 mm wide, 9.53 mm wide, or 11.48 mm wide. In the implementations in which curved corners are utilized, the radius of the corners may be approximately 12.7° or a range from 12° to 13°. In some cases, the slope of the taper of the first wide region of the interior section from the maximum width to the width of the narrow leg region of the interior section may be approximately 31.75° or between 30° and 32°.

In some implementations, the width of the first wide region of the concave depression may be expressed as a ratio with respect to the narrow region of the concave depression. For example, the first wide region of the concave depression may be 3 times the width of the narrow region of the concave depression at the widest point. In another example, the ratio may be approximately 4 to 1. In some cases, the ratio may be greater than 3:1 or greater than 4:1.

In some cases, the second wide region of the concave depression may generally have the shape of an arrowhead. In another implementation, the second wide region of the concave depression may vary from 52.06 mm to 12.7 mm wide. In another example, the second wide region of the concave depression in the top sheet may, in some implementations, vary from 56.37 mm to 19.06 mm wide. For instance, the tip of the arrowhead shape may be 19.06 mm wide and the base of the arrowhead shape may be 56.37 mm wide. In other cases, the tip of the arrowhead may be between 6 mm and 15 mm wide and the base of the arrowhead may be between 12 mm and 20 mm and the base of the arrowhead may be between 52 mm and 57 mm. In one specific implementation, the tip of the arrowhead may be between 9 mm and 25 mm wide and the base of the arrowhead may be between 50 mm and 60 mm.

In some implementations, the width of the second wide region of the concave depression may be expressed as a ratio with respect to the narrow region of the concave depression. For example, the second wide region of the concave depression may be 3 times the width of the narrow region of the concave depression at the widest point. In another example, the ratio may be approximately 4 to 1. In some cases, the ratio may be greater than 3:1 or greater than 4:1. Additionally, the first wide region of the concave depression may be expressed as a ratio of the second wide region of the concave depression. In this example, the first wide region of the concave depression may be 1.2 times the width of the second wide region of the concave depression at the narrowest point of both. In other example, the first wide region of the concave depression may be 2 times the width of the second wide region of the concave depression at the narrowest point of both. Likewise, the second wide region of the concave depression may be 1.1 or 1.2 times the width of the first wide region of the concave depression. In other example, the first wide region of the concave depression may be 1 time the width of the second wide region of the concave depression at the widest point of both.

In some cases, the length of the concave depression may also have a length that is less than the length of the top sheet of the liner (e.g., the concave depression does not extend from the front to the back of the top sheet). For example, as discussed above, the top sheet may be approximately 261.51 mm long and the concave depression may be approximately 216.76 mm long. In another example, the concave depression may be less than 220 mm long. In some cases, the concave depression may vary between 180 mm long and 220 mm long.

In the present examples, the concave depression may be configured to be a first predetermined distance from a front end of the top sheet and a second predetermined distance form the back end of the top sheet. In some examples, the first predetermined distance may be 11.86 mm, 12 mm, or a value between 10 and 12 mm from the front of the top sheet. In some examples, the second predetermined distance may be 19.04 mm, 19 mm, or a value between 18 and 22 mm from the back of the top sheet.

Similarly, the concave depression may maintain a third predetermined distance from the first side of the top sheet and a fourth predetermined distance form the second side of the top sheet. In some case, the third predetermined distance and the second predetermined distance may be the same. For example, the third predetermined distance and the fourth predetermined distance may be 20.27 mm or 22.22 mm. In some case, the third predetermined distance and the fourth predetermined distance may be between 20 mm and 25 mm or between 18 mm and 30 mm. In some cases, the concave depression may encompasses the entirety of the top sheet, such that the entire top sheet is formed form hydrophilic material.

Further, it should be understood that the potty training liner discussed herein is not for use while swimming or other water sports. Thus, the potty training liner is not configured for use as swim pants. Additionally, the potty training liner does not include a leg hole or other means of forming a leg hole as in conventional potty training garments. Rather, the potty training liner discussed herein is to be used in conjunction with conventional under garments, such as underwear. In some examples, the potty training liner may include an adhesive layer applied to the exterior of the back sheet. The adhesive layer may include a paper or other removable protective layer over the adhesive.

FIG. 1 illustrates an example top view of the potty training liner 100 according to some implementations. In the current example, the potty training liner may be configured to be worn or used in conjunction with an undergarment (such as underwear). For instance, the potty training liner may be configured to adhere or otherwise secure to the inside of the undergarment during use. In this manner, the undergarment holds the potty training liner in contract with the child's skin during use but allows the child to wear underwear or "grown up" undergarments, which allows the child to make the mental leap to differentiate a diaper or other potty training garments, thereby encouraging success during potty training.

In the illustrated example, the potty training liner 100 includes a back sheet 102, a top sheet 104, and an interior section. The top sheet 104 includes an area, generally indicated by 108, that allows for fluid within a channel, generally indicated by 110, to be absorbed by the interior section. In some examples, the area 108 may be an concave depression exposing the interior section to the skin of a user or wearer, while in other examples, the area 108 may be hydrophilic and the remainder of the channel 110 may be hydrophobic.

In an alternative example, the area 108 may be hydrophobic, while the remainder of the area exposed within the channel 110 is hydrophilic. For example, the area 108 may be treated by a hydrophobic or waterproof glue or ink to prevent fluid from wicking too quickly in the middle of the channel 110. Thus, in this example, the fluid would move back and forth over the area 108 until the fluid was passed to the interior section via the exterior area of the channel 110. In this alternative example, the area 108 may cover approximately 95%, 90%, 85%, 80%, 75%, or 50% of the channel 110.

The channel 110 is formed around the area 108. The channel 110 may be bounded on both sides by a channel wall 112 and 114. The channel 110 may be configured to allow fluid, such as urine, to traverse back and forth within the channel 110 during a period of time associated with absorption. For example, the channel 110 may channel or otherwise cause the fluid to distribute within the channel 110 as the child moves. In some cases, the period of time associated with absorption may be greater than 2 minutes, greater than 5 minutes, greater than 10 minutes, greater than 15 minutes or greater than 20 minutes.

In some cases, as discussed above the interior section and/or the potty training liner 100 may be configured to absorb less fluid (e.g., urine) than is associated with a common or averaged size child's bladder. For instance, the interior section and/or the potty training liner 100 may be configured to absorb 40 ml or less of fluid, 60 ml or less of fluid, 80 ml or less of fluid, 100 ml or less of fluid, or 200 ml or less of fluid.

In general, the channel walls 112 and 114 may be positioned at a predetermined distance from the edge of the potty training liner 100. For instance, the predetermined minimum distance, generally indicated by 116 and 118, from the edge of the potty training liner 100 may be greater than greater than 10 mm from the edge of the potty training liner 100, greater than 15 mm from the edge of the potty training liner, greater than 20 mm from the edge of the potty training liner 100, or greater than 25 mm from the edge of the potty training liner 100. The channel walls 112 and 114 may also be positioned to have a maximum predetermined distance from the edge of the potty training liner 100. For example, the maximum predetermined distance, generally indicated by 120 and 122, may be greater than 20 mm from the edge of the potty training liner 100, greater than 25 mm from the edge of the potty training liner 100, greater than 30 mm from the edge of the potty training liner 100.

The channel walls 112 and 114 may also be configured to maintain a predetermined distance, generally indicated by 124 and 126, from the interior or center line of the potty training liner 100. For example, the channel walls 112 and 114 may be approximately 17.43 mm from the center line of the potty training liner 100 on each side. In some cases, the channel walls 112 and 114 may be between 17 mm and 18 mm from the center line of the potty training liner 100. Thus, the channel 110 may be approximately 34 mm wide or between 30 mm and 40 mm wide.

Figure 2:
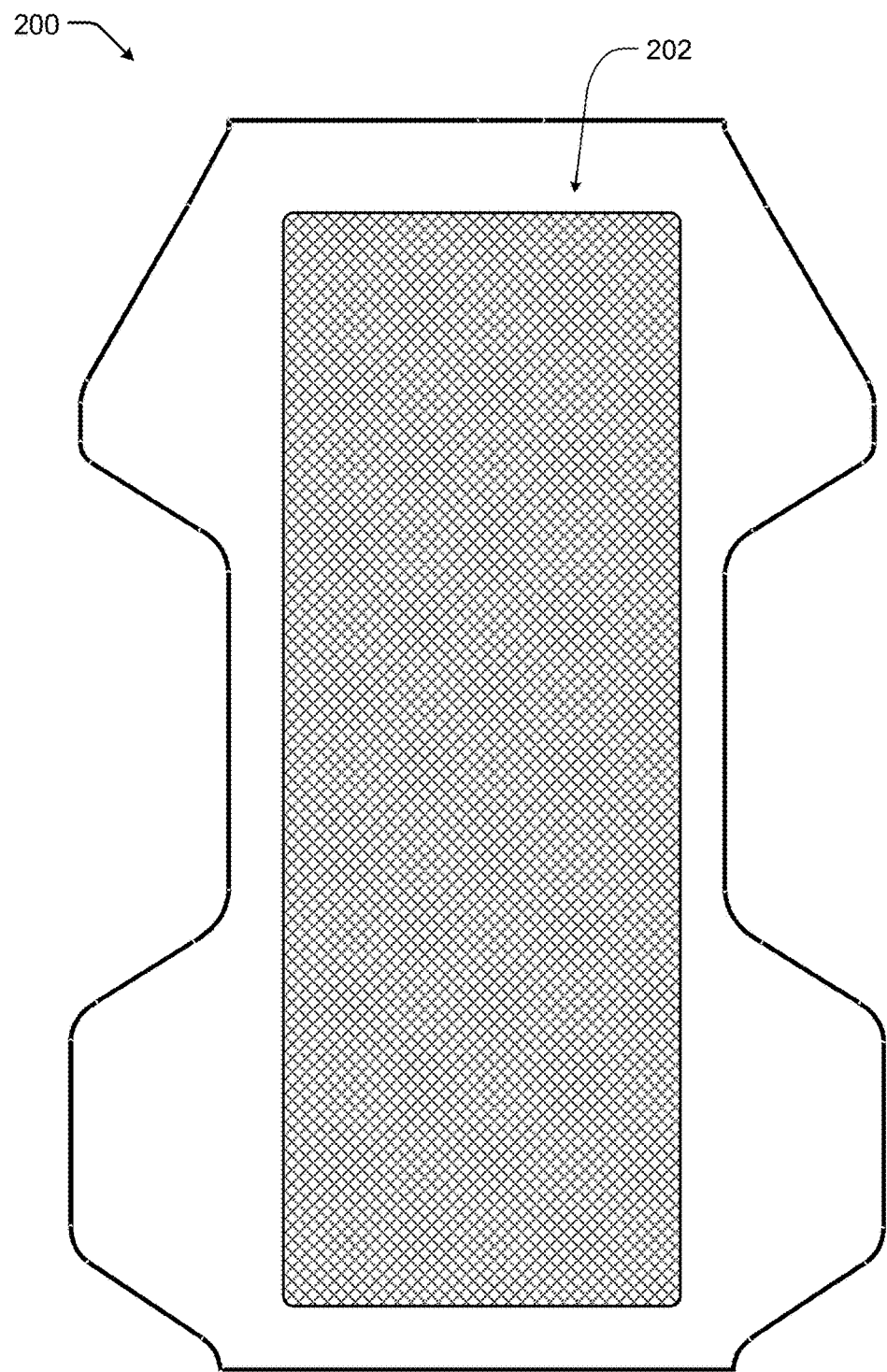
FIG. 2 illustrates an example bottom view of the potty training liner according to some implementations.

In the current example, the potty training liner 100 is configured such that the potty training liner 100 does not close or seal. In this manner, the potty training liner 100 remains open around the legs of the user when the potty training liner 100 is worn (or in use) and is still able to leak or cause the undergarments of the child to become wet or messy. In this example, this situation is acceptable as a moderate wetting of the undergarments can be a useful tool in potty training a child. In particular, the risk of wetting an undergarment increases with increased duration of wear following an incident or accident by the child (e.g., the longer the child wears the wet liner 100 the more likely the child's undergarments are to become wet or dirty). FIG. 2 illustrates an example bottom view of the potty training liner 200 according to some implementations. The potty training liner 200 may be the same as the potty training liner 100 but as viewed from the opposite direction (e.g., as viewed from the back or bottom). In this example, the potty training liner 200 may include an adhesive layer 202 applied to a surface of a back sheet 204. The adhesive layer 202 may be configured to releasably couple the potty training liner 200 to an undergarment (e.g., 23 underwear) of a child. In some cases, the adhesive layer 202 may be covered or protected by a removable paper or protective layer, such as a release strip (not shown).

In the current example, the surface of the back sheet 204 shown is exposed to the environment during use (e.g., the surface is exposed to the undergarment or the surface is opposite the surface of the potty training liner 200 in contact with the skin of the wearer). The back sheet 204 may be formed from a hydrophobic or water repellant material. In some cases, the back sheet 204 may be formed from a polyethylene film or nonwoven laminate.

As illustrated, the potty training liner 200 may be configured to operate only in conjunction with an undergarment. For example, the potty training liner 200 may fall off or otherwise disengage if a child attempts to wear the liner 200 without the aid of an undergarment. Additionally, the potty training liner 200 may, in some cases, to operate in dry conditions (e.g., the user of the potty training liner 200 with swim wear may result in failure as the adhesive layer 202 may be rendered ineffective when wet and cause the potty training liner 200 to slip or become misaligned during use).

Figure 3:
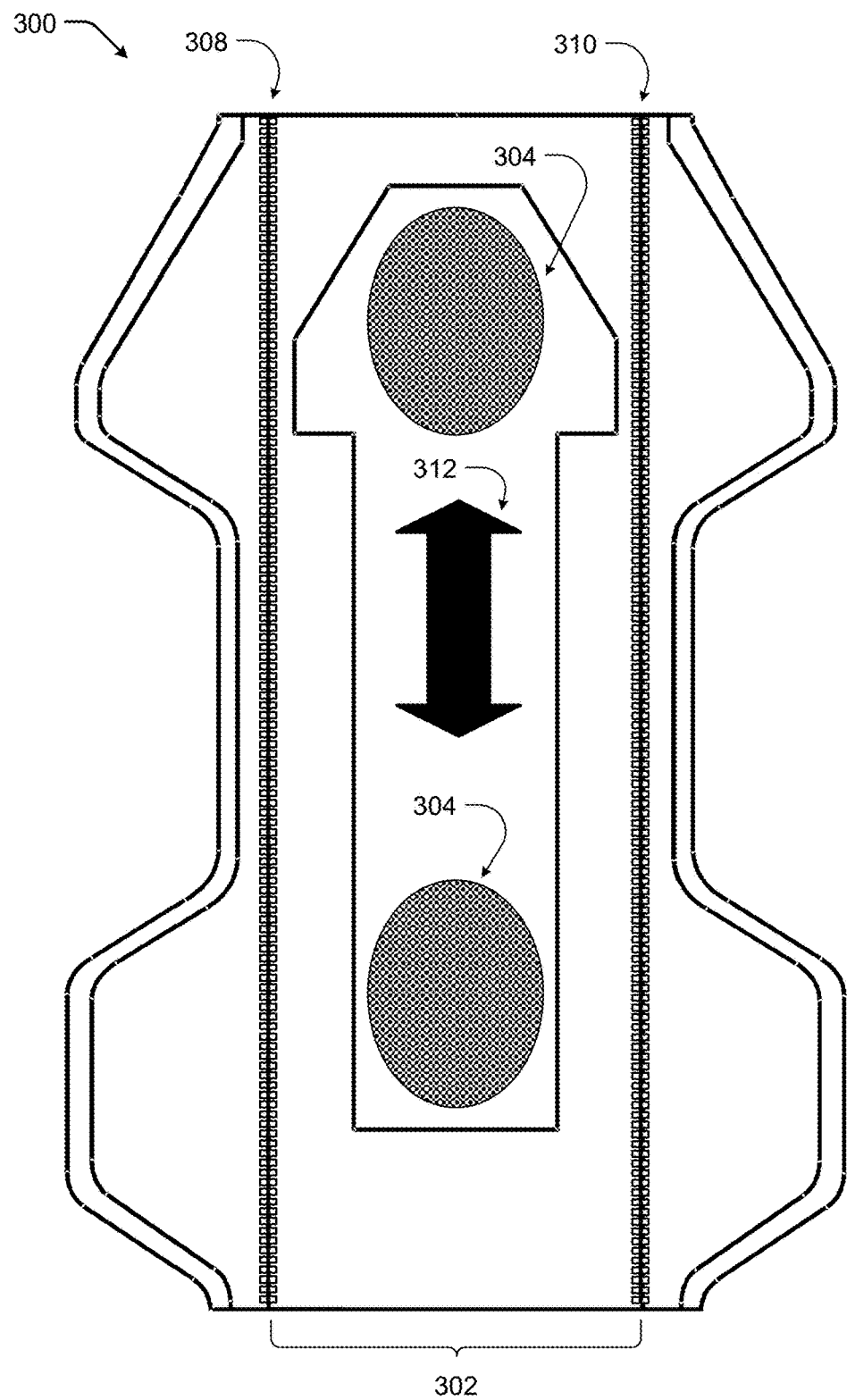
FIG. 3 illustrates another example top view of the potty training liner according to some implementations.

FIG. 3 illustrates another an example top view of the potty training liner 300 according to some implementations. In this example, a channel 302 of the potty training liner 300 may include one or more hydrophilic areas 304 while the remainder of the channel 302 is hydrophobic. In this manner, the channel 302 may cause the fluid to move back and forth in response to movement of the child and, in this example, to be absorbed by the interior section at the front and rear areas but not along the middle. In an alternative example, the hydrophilic areas 304 and the hydrophobic areas may be reversed. Further it should be understood, that in other examples, the number and positions of the hydrophilic areas 304 and the hydrophobic areas may be in any arrangement or position within or above the interior section.

In the illustrated example, following an insult or accident, the fluid (e.g., urine) within the channel 306 formed by the channel walls 308 and 310 may be forced to move from front to back along the direction indicated by arrow 312 as the fluids are absorbed. In this manner, the child or wearer of the potty training liner 300 may experience discomfort as the fluid moves against their skin. Additionally, by allowing only select hydrophilic areas 304, the rate of absorption of even a small insult or accident may be increased to further encourage the child to go to the potty. For example, the interior section 302 may not become fully statured for a period of greater than 60 seconds, 2 minutes, greater than 5 minutes, greater than 10 minutes, greater than 15 minutes, or even greater than 20 minutes. Further, it should be understood, in some examples the interior section 302 and/or the entire potty training liner 300 may be configured to absorb less than an amount of liquid associated with an average insult. For example, the potty training liner 300 may be configured to absorb less than 40 ml, less than 60 ml, less than 80 ml, less than 100 ml, less than 150 ml, or less than 200 ml.

In some examples, the absorption capacity may be a ratio of the size of the potty training liner 300. For example, the absorption rate of the interior section 302 may be approximately ⅙ of the length of the potty training liner 300. For instance, if the potty training liner is 261 mm long, the interior section may absorb 40 ml of liquid. In another example, the absorption rate may be approximately ¼ the length of the potty training liner 300, ⅓ the length of the potty training liner 300, or approximately 0.8 times the length of the potty training liner 300. In another example, the absorption capacity may be a ratio of the size of the interior section 302. For example, the absorption rate of the interior section 302 may be approximately ⅕ of the length of the potty training liner 300. In another example, the absorption rate may be approximately ¼ the length of the potty training liner 300, ½ the length of the potty training liner 300, or approximately 0.8 times the length of the potty training liner 300.

Figure 4:
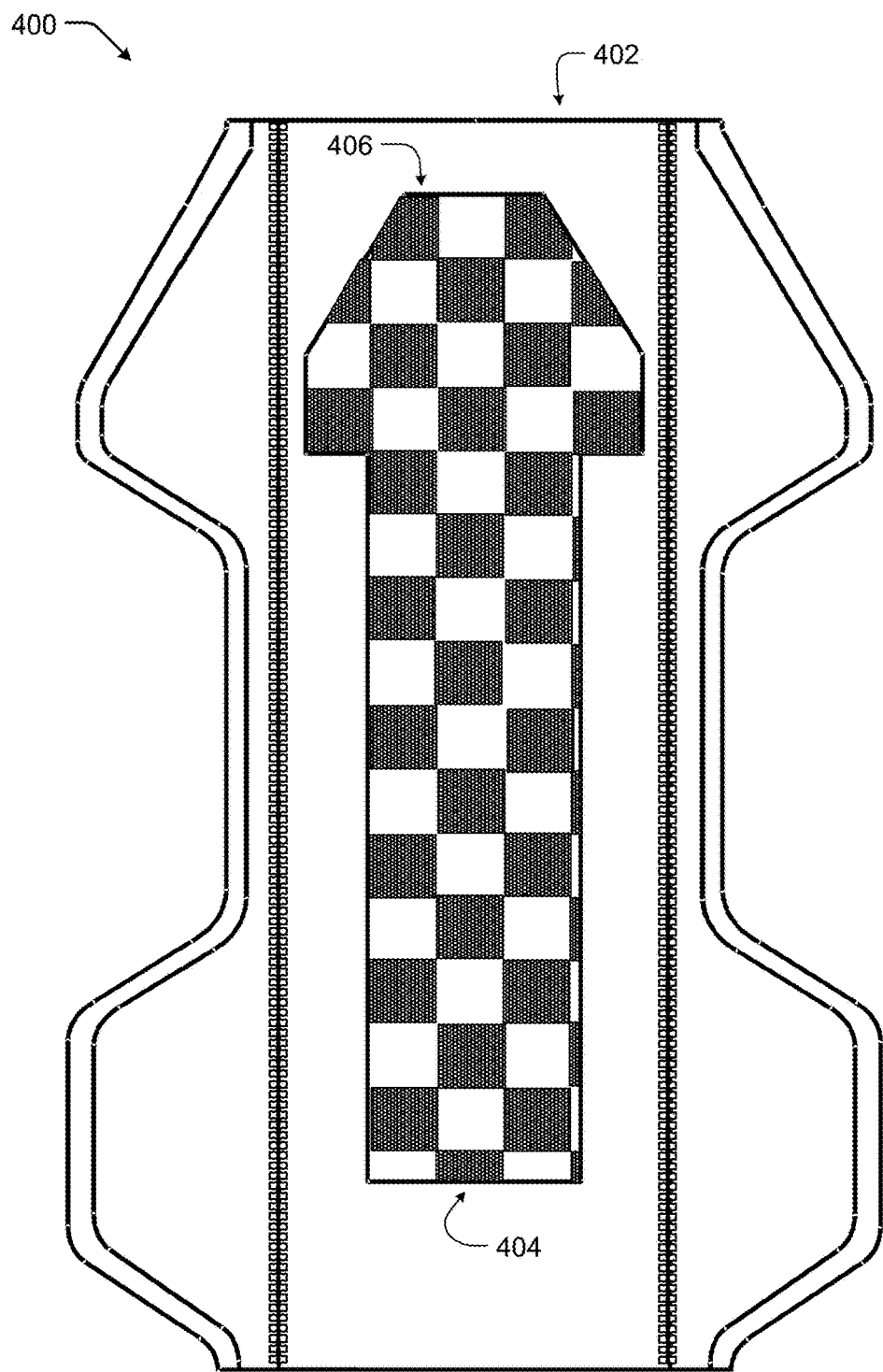
FIG. 4 illustrates yet another example top view of the potty training liner according to some implementations.

FIG. 4 illustrates yet another an example top view of the potty training liner 400 according to some implementations.

In the current example, the channel 402 of the potty training liner 400 may include alternating hydrophilic areas 404 (e.g., the dark areas) and hydrophobic 406 (e.g., the light areas). In the illustrated example, the alternating of the hydrophilic areas 404 and hydrophobic areas 406 may both slow the rate of absorption of the insult or accident and extend the time it takes to fully absorb the insult or accident. Additionally, the alternating of the hydrophilic areas 404 and hydrophobic 406 cause the wearer or child to experience sensation of movement of the liquid as the liquid moves over the hydrophobic areas 406, thereby making the child aware of the accident.

Figure 5:
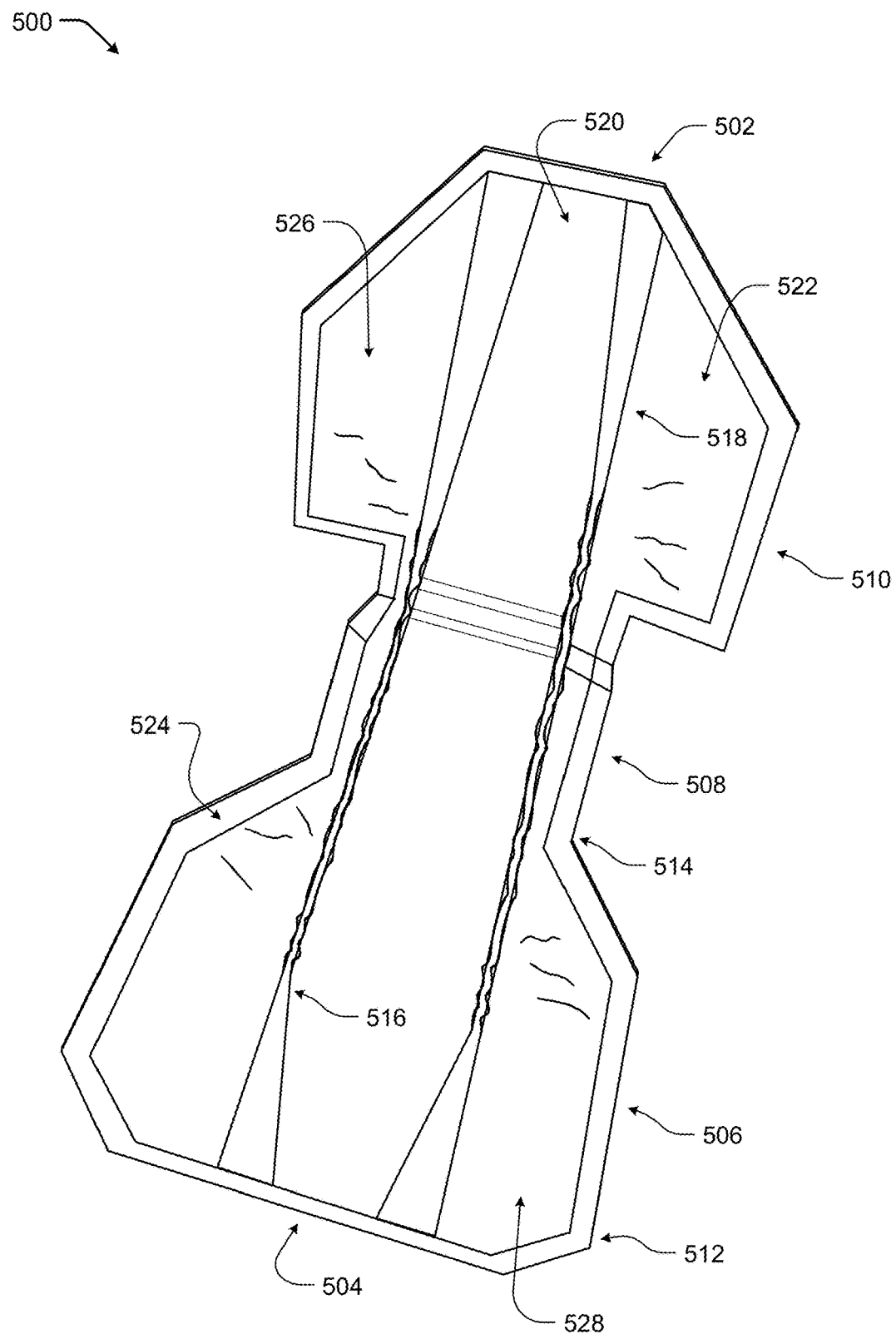
FIG. 5 illustrates an example pictorial top view of the potty training liner according to some implementations.

FIG. 5 illustrates an example pictorial top view of the potty training liner 500 according to some implementations. The potty training liner 500 may be configured to fit between the skin of the user and undergarments. Thus, the potty training liner 500 is in direct contact with the skin of the user or child during use. The potty training liner 500 may be thin, while the conventional potty training garment is typically greater than 10 mm thick. In some implementations, the dry thickness of the potty training liner 500 may be less than 10 mm thick, less than 8.0 mm thick, less than 5.0 mm thick, less than 1.0 mm thick, or less than 0.7 mm thick. In some cases, the potty training liner 500 may be between 276 mm long and 245 mm long from a front end 502 to a back end 504. The potty training liner 500 may also have a folded thickness of less than 15 mm, 10 mm, less than 5.0 mm, less than 3.0 mm or less than 2.0 mm, while conventional potty training garments typically have a folded thickness of greater than 20 mm. Thus, the conventional potty training garment have a bulky "diaper like" feel to them, like the traditional diapers a child has worn since birth, while the potty training liner 500 has a more lightweight feel.

The potty training liner 500 may also have a roughly arrow like shape that includes a first wide region 506 (e.g., near the back end 504), a narrow region 508 (e.g., the leg region), and a second wide region 510 (e.g., near the front end 502). As discussed above, the first wide region 506 may generally have the shape of the first the arrow fletching. In some implementations, the fletching shape may include corners, while in other cases, the fletching shape may include curved corners to improve the ease of manufacturing. In some cases, the length of the first wide region 506 may be 85.76 mm. In some examples, the length of the first wide region 506 may be between 80 mm and 100 mm or between 85 mm and 90 mm.

The first wide region 506 may, in some implementations, vary from 101.6 mm to 63.5 mm wide. In another example, the first wide region 506 may have a maximum width (e.g., at the location generally indicated by 512) of between 90 mm and 105 mm and a minimum width (e.g., at location generally indicated by 514) of between 55 mm and 70 mm. In one example, the first wide region 506 may gradually slope inward from the maximum width to the width of the narrow region 508 (e.g., at location 514).

In some cases, the narrow region 508 may vary from 62 mm wide to 64 mm wide. In some specific examples, the narrow region 508 may be 63.5 mm wide. In the implementations in which curved corners are utilized, the radius of the corners may be approximately 12.7° or a range from 12° to 13°. In some implementations, the width of the first wide region 506 may be expressed as a ratio with respect to the narrow region 508. For example, the first wide region 506 may be 1.6 or 1.5 times the width of the narrow region 508 at the widest point. The narrow region 508 may have a length of 76.17 mm or approximately 76 mm. In some examples, the length of the narrow region 508 may be between 75 mm and 80 mm, between 70 mm and 85 mm, or between 70 mm and 85 mm.

In some cases, the second wide region 510 may generally have the shape of an arrowhead. In another implementation, the second wide region 510 may vary from 101.6 mm to 63.5 mm wide. For instance, the tip of the arrowhead shape may be 63.5 mm wide and the base of the arrowhead shape may be 101.6 mm wide. In other cases, the tip of the arrowhead may be between 60 mm and 65 mm wide and the base of the arrowhead may be between 100 mm and 105 mm. In some implementations, the width of the second wide region 510 may be expressed as a ratio with respect to the narrow region 508. In some cases, the length of the second wide region 510 may be 85.73 mm or approximately 85 mm.

In some implementations, the potty training liner 500 may include a first and second channel wall 516 and 518 that extends the full length of the potty training liner 500 from a front end 502 to a back end 504, as shown. For example, the liner 500 may be 247.66 mm long and the channel walls 516 and 518 may also be 247.66 mm long. In other words, each of the channel walls 516 and 518 extend the entire length of the potty training liner 500 at a full height or above a particular minimum height. In some cases, the channel walls 516 and 518 may be formed from an elastic yarn and a hydrophobic polyethylene material. The channel walls 516 and 518 may be designed to cause fluid within the potty training liner 500 to channel from the front end 502 to the back end 504 and vice versa. Thus, the channel walls 516 and 518 may each extend upwards from the base or interior section of the potty training liner 500 for the entire length of the liner 500.

In some cases, each of the channel walls 516 and 518 may be greater than 1.0 inches tall. In other cases, the channel walls 516 and 518 may be greater than 1.5 inches tall. In a specific case, the channel walls 516 and 518 may be greater than or equal to 2.0 inches tall. In some instances, the channel walls 516 and 518 may vary from half an inch to one inch tall, such that the channel walls 516 and 518 is shorter near the front end 502 and the back end 504 than in the middle of the potty training liner 500. In one example, the channel walls 516 and 518 may be approximately 4 mm wide. In another instance, the channel walls 516 and 518 may be less than 4 mm wide. In still other instances, the channel walls 516 and 518 may be less than 5 mm wide or less than 6 mm wide.

The channel walls 516 and 518 may also be configured to maintain a predetermined distance from the side of the potty training liner 500. For example, the channel walls 516 and 518 may be greater than 29 mm from the side of the potty training liner 500, at for instance location 512, and greater than 10 mm from the side of the potty training liner 500, at for instance location 514. Thus, the channel walls 516 and 518 may be greater than 10 mm form the side of the potty training liner 500 for the full length of the liner. In another example, the channel walls 516 and 518 may be greater than 12 mm from the side of the potty training liner or greater than 15 mm from the side of the potty training liner 500. In this example, the placement of the channel walls 516 and 518 at the predetermined distance from the side of the potty training liner 500 and the height of the channel walls 516 and 518 allows the potty training liner 500 to form a channel 520 that allows fluid to move forward and backwards within the channel 520 (e.g., the space between the channel walls 516 and 518).

Each of the channel walls 516 and 518 may also be configured to maintain a predetermined distance from the interior or center line (not shown) of the potty training liner 500. For example, the channel walls 516 and 518 may be approximately 17.43 mm from the center line of the potty training liner 500. In some cases, the channel walls 516 and 518 may be between 17 mm and 18 mm from the center line of the potty training liner 500.

The potty training liner 500 may also include a top sheet 522 and a back sheet 524. The top sheet 522 may be 16 gsm and have a dry thickness of 0.112 mm. Likewise, the back sheet 524 may be 0.07 mm thick and 9 gsm. The top sheet 522 may and back sheet 524 may have width and length dimensions that are substantially similar to the overall potty training liner 500. For example, the top sheet 522 and back sheet 524 may also have the substantially arrow shape with a first wide region 506, a narrow region 508, and a second wide region 510.

In some cases, the first wide region 506 of the top sheet 522 or back sheet 524 may be 85.76 mm long. In some examples, the length of the first wide region 506 of the top sheet 522 or back sheet 524 may be between 80 mm and 100 mm or between 85 mm and 90 mm. The first wide region 506 of the top sheet 522 or back sheet 524 may, in some implementations, vary from 101.6 mm to 63.5 mm wide. In another example, the first wide region 506 of the top sheet 522 or back sheet 524 may have a maximum width of between 90 mm and 105 mm and a minimum width of between 55 mm and 70 mm. In one example, the first wide region 506 of the top sheet 522 or back sheet 524 may gradually slope inward from the maximum width to the width of the narrow region 508.

In some cases, the narrow region 508 of the top sheet 522 or back sheet 524 may vary from 62 mm wide to 64 mm wide. In some specific examples, the narrow region 508 may be 63.5 mm wide. In the implementations in which curved corners are utilized, the radius of the corners may be approximately 12.7° or a range from 12° to 13°. In some implementations, the width of the first wide region 506 of the top sheet 522 or back sheet 524 may be expressed as a ratio with respect to the narrow region 508 of the top sheet 522 or back sheet 524. For example, the first wide region 506 may be 1.6 or 1.5 times the width of the narrow region 508 at for instance location 512. The narrow region 508 may have a length of 76.17 mm or approximately 76 mm. In some examples, the length of the narrow region 508 of the top sheet 522 or back sheet 524 may be between 75 mm and 80 mm, between 70 mm and 85 mm, or between 70 mm and 85 mm.

In some cases, the second wide 510 region of the top sheet 522 or back sheet 524 may generally have the shape of an arrowhead. In another implementation, the second wide region 510 of the top sheet 522 or back sheet 524 may vary from 101.6 mm to 63.5 mm wide. For instance, the tip of the arrowhead shape may be 63.5 mm wide and the base of the arrowhead shape may be 101.6 mm wide. In other cases, the tip of the arrowhead may be between 60 mm and 65 mm wide and the base of the arrowhead may be between 100 mm and 105 mm. In some implementations, the width of the second wide region 510 of the top sheet 522 or back sheet 524 may be expressed as a ratio with respect to the narrow region 508. In some cases, the length of the second wide region 510 of the top sheet 522 or back sheet 524 may be 85.73 mm or approximately 85 mm.

In some implementations, the top sheet may also include an concave depression (not shown) again having an arrow shape to expose the interior section to the liquids associated with an insult or accident. However, in the current example, the concave depression may be the entire area of the channel 520. Thus, the interior section may be exposed within the channel 520 but protected along the exterior areas 526 and 528 by the top sheet 522 and the back sheet 524 (e.g., the interior section may be laminated or otherwise coupled between the top sheet 522 and the back sheet 524 during assembly).

Additionally, while the lengths and widths of the top sheet 522 and the back sheet 524 have been discussed as substantially similar, in some case, such as the illustrate example, the back sheet 524 may be longer and/or wider than the top sheet 524.

Figure 6:
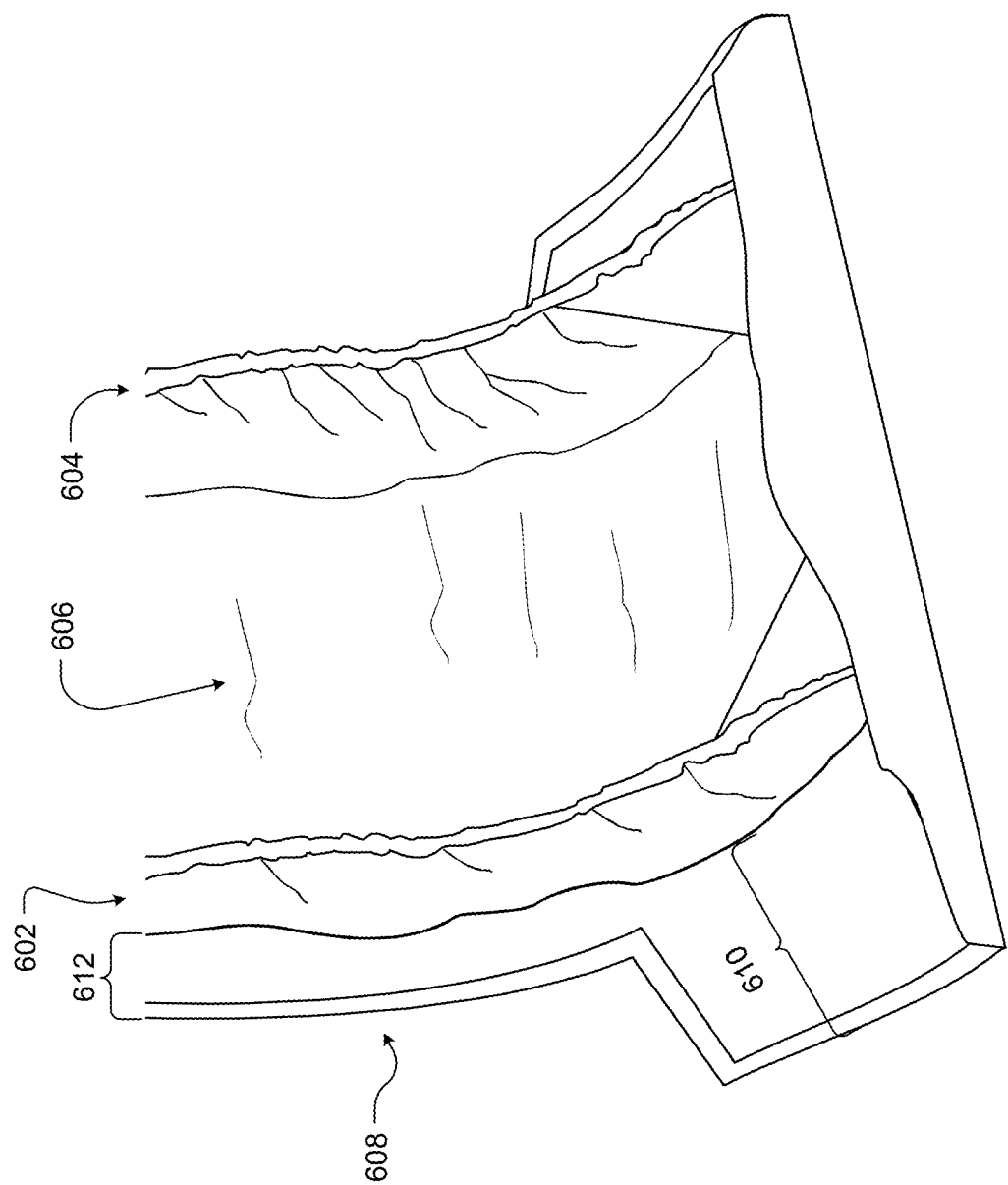
FIG. 6 illustrates an example partial pictorial view of the potty training liner according to some implementations.

FIG. 6 illustrates an example partial pictorial view of the potty training liner 600 according to some implementations. In the current example, a first and second channel walls 602 and 604 are shown positioned as if during use. As illustrated, the first and second channel walls 602 and 604 form the channel 606 in which the fluid associated with an accident or insult may be maintained. As shown, the channel walls 602 and 604 may maintain a height from the top sheet from the front end to the back end of the potty training liner 600. In some cases, the channel walls 602 and 604 may be formed from one or more hydrophobic layers, one or more elastic layers as well as one or more adhesive layers to bound the hydrophobic layers and the elastic layers together and/or to bond the channel walls 602 and 604 to the potty training liner 600.

In some cases, each of the channel walls 602 and 604 may be greater than 1.0 inches tall. In other cases, the channel walls 602 and 604 may be greater than 1.5 inches tall. In a specific case, the channel walls 602 and 604 may be greater than or equal to 2.0 inches tall. In one example, the channel walls 602 and 604 may be approximately 4.0 mm wide. In another instance, the channel walls 602 and 604 may be less than 4.0 mm wide. In still other instances, the channel walls 602 and 604 may be less than 5.0 mm wide or less than 6.0 mm wide.

As shown in the illustrated example, the channel walls 602 and 604 may maintain a minimum distance from the side edge 608 of the potty training liner 600. For example, the channel walls 602 and 604 may be greater than 29 mm from the side of the potty training liner 600, as generally indicated by 610, and greater than 10 mm from the side of the potty training liner 600, generally indicated by 612. Thus, the channel walls 602 and 604 may be greater than 10 mm form the side of the potty training liner 600 for the full length of the liner 600. In another example, the channel walls 602 and 604 may be greater than 12 mm from the side of the potty training liner 600 or greater than 15 mm from the side of the potty training liner 600. In other cases, the channel walls 602 and 604 may be greater than 5 mm from the side 608 of the liner 600.

In one specific example, the channel walls 602 and 604 may be formed from a stair step or pyramidal or stair-step fashion. For example, the channel walls 602 and 604 may be three layers of stacked absorbent and/or superabsorbent material. The layers of the channel walls 602 and 604 are made of three layers, a bottom layer 13, a middle layer 12 and top layer that, when compressed between the thigs of the wearer in use, create, 602 or 604, maintains a channel void space in the center channel area to encourage urine flow through the channel to the front and rear of the potty training liner 600.

Figure 7:
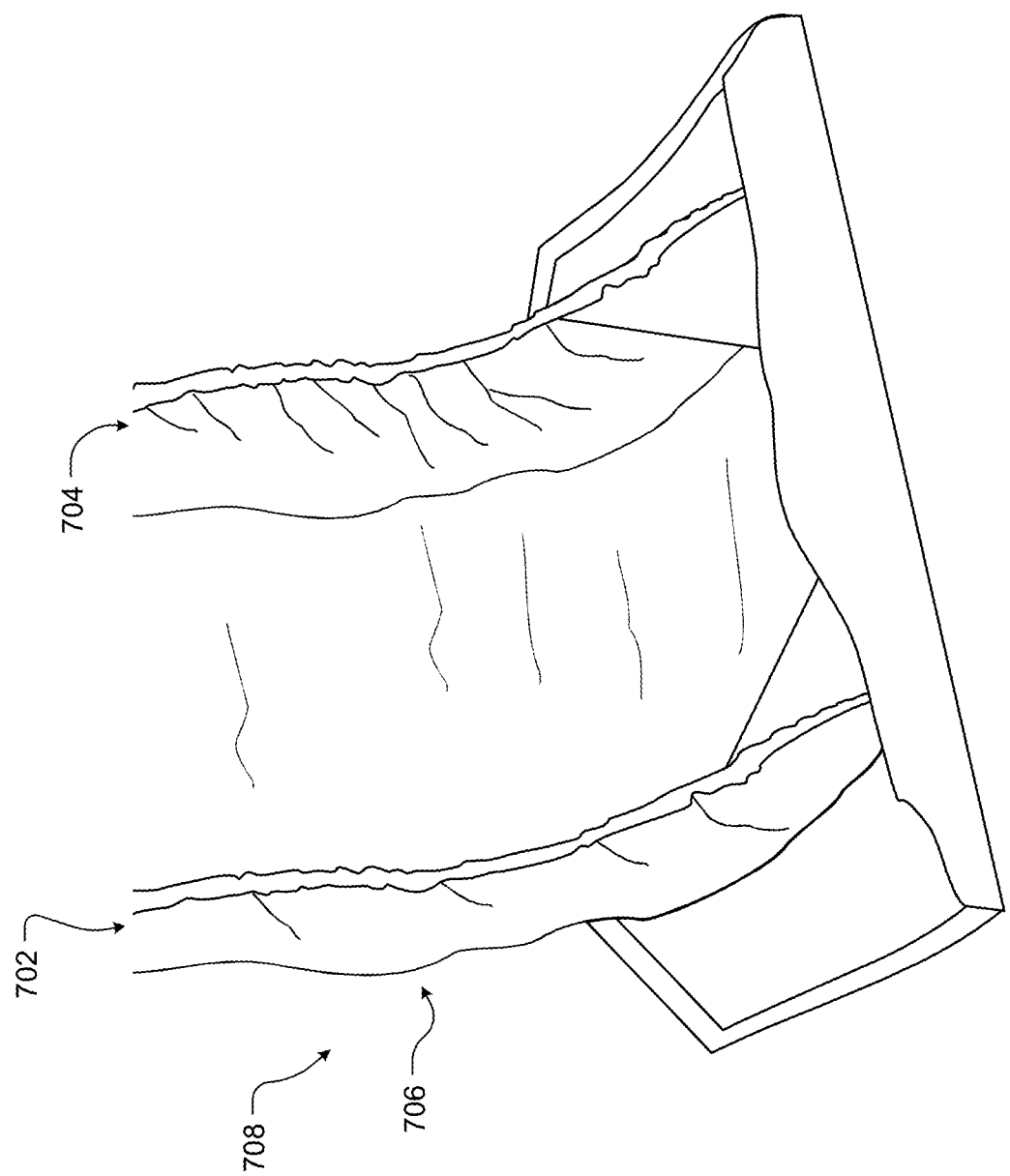
FIG. 7 illustrates another example partial pictorial view of the potty training liner according to some implementations.

FIG. 7 illustrates another example partial pictorial view of the potty training liner 700 according to some implementations. In this example, similar to the example of FIG. 6 above, the channel walls 702 and 704 may maintain a predetermined height for the entire length of the liner 700 from the front end to the back end. However, in this example, unlike the example of FIG. 6, the channel walls 702 and 704 may be along the side edge, such as edge 706, of the potty training liner 700 at the narrow region, generally indicated by 708, of the potty training liner 700.

Figure 8:
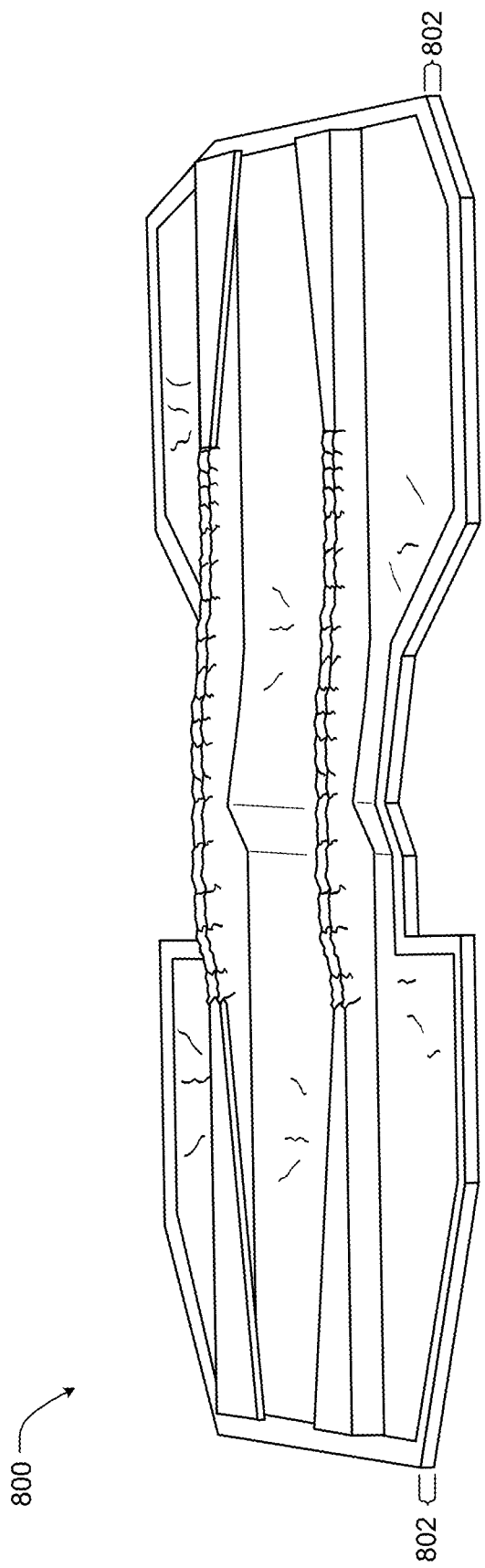
FIG. 8 illustrates an example pictorial side view of the potty training liner according to some implementations.

FIG. 8 illustrates an example pictorial side view of the potty training liner 800 according to some implementations. In this example, the relative thinness or reduced dry thickness of the potty training liner 800 is shown. For example, the potty training liner 800 may have a dry thickness, generally indicated by 802, of less than 4.0 mm, 5.0 mm, less than 6.0 mm, less than 7.0 mm, less than 8.0 mm, or less than 10.0 mm. For example, since the interior section (not shown) is designed to absorb less than a single bladder's worth of liquid (e.g., less than 40 ml, less than 60 ml, less than 80 ml, or less than 100 ml of liquid), the relative dry thickness of the interior section may be reduced when compared with conventional potty training garments. For example, the interior section may be less than 0.1 mm thick, less than 0.3 mm thick, or less than 0.5 mm thick. In some cases, the interior section may be formed from airlaid nonwoven material, ADL, and SAP paper. In some cases, the length wise folded thickness of the potty training liner 800 may be less than 1.5 inches thick or less than 2.0 inches thick, while conventional potty training liners are typically 3 inches thick or greater when folded lengthwise.

Figure 9:
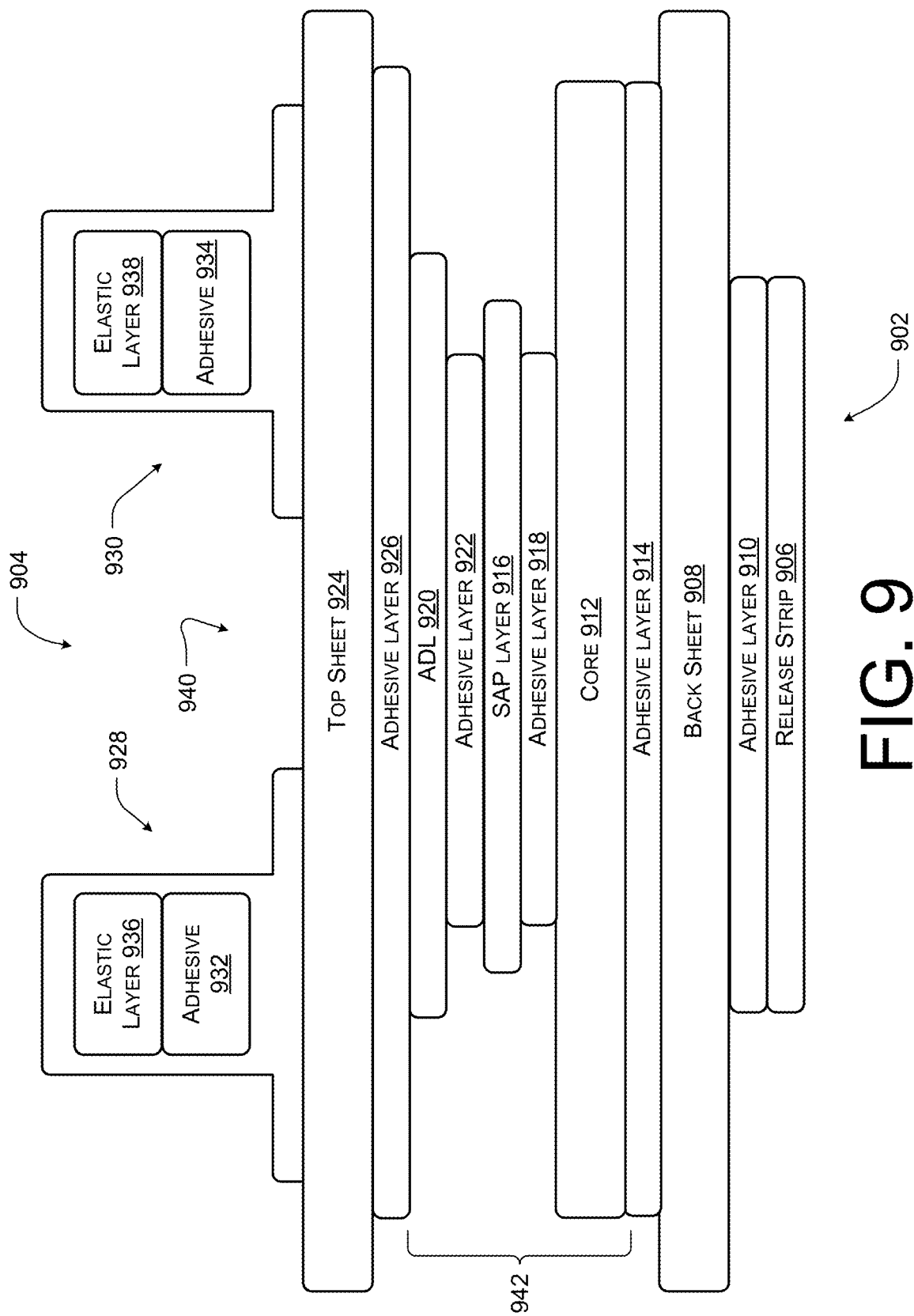
FIG. 9 illustrates example cross sectional view of a potty training liner according to some implementations.

FIG. 9 illustrates example cross sectional view of a potty training liner 900 according to some implementations. In the current example, the area generally indicated by 902 may be the bottom side of the potty training liner 900 or the side exposed to the undergarment of the wearer. Likewise, the area, generally indicated by 904, may be the top side of the potty training liner 900 or the area in contact with the skin of the wearer. In some cases, the liner 900 is machine-shaped into the configuration shown. The machine-shaping may include one or more adhesive applications including curing steps as well as one or more cutting steps to remove excess material.

In the current example, starting at the bottom 902, a release strip 906 may be releasably coupled to a back sheet 908 via an achieves layer 910. In this example, the release strip 906 may be configured to be removed from the back sheet 908 to expose the adhesive layer 910, such that the adhesive layer 910 may be used to secure the potty training liner 900 to an undergarment (such as underwear). In some cases, the back sheet 908 may be formed from a polyethylene film, nonwoven laminate, or combination thereof. In some instances, the back sheet 908 may be 0.07 mm thick or less.

The potty training liner 900 may also have an interior section 942 atop the back sheet 908. The interior section 942 may in turn be formed by multiple layers. For instance, in the current example, the interior section 942 may include a core 912 be positioned atop the back sheet 908 and secured to the back sheet 908 via an adhesive layer 914. The core 912 may be less than 0.1 mm or less than 0.2 mm thick and formed from an airlaid SAF material or airlaid SAP material. In some cases, the core 912 may be formed from a fibrous matrix of cotton or wood pulp fluff which may be enhanced with a high-absorbency material or superabsorbent. Superabsorbents may be crosslinked polymers capable of absorbing 10 to 100 times their weight in water. Superabsorbents may also be formed from various laminate structures. For example, a laminate superabsorbent material may include a layer of discrete discontinuous elements attached to a continuous porous support layer. The superabsorbent may be formed by saturating a porous substrate with an acrylic, such as, for example, an acrylic acid monomer solution. The monomer may then be polymerized and crosslinked in the monomer web, thereby allowing the resultant superabsorbent material to absorb a desired fluid. In the present disclosure, the superabsorbent is designed to absorb a water-based fluid, such as urine.

In the current example, a super absorbent polymer (SAP) layer 916 may be placed atop the core 912 as part of the interior section 942. The SAP layer 916 may also be secured to the core 912 via an adhesive layer 918. In some cases, the SAP layer 916 may be formed from paper impregnated with a SAP. The SAP may be a hydrophilic polymer made of fine particles of an acrylic acid derivative, such as sodium acrylate, potassium acrylate, or an alkyl acrylate. In the current example, the SAP layer 916 is placed over the core 912 unlike conventional diapers or sanitary pads which place the SAP layer under the core 912. In some cases, the SAP layer 916 may from a gel block or hydrophobic layer as the absorbents in the SAP layer 916 absorb fluid. The gel blocking may then prevent additional fluid from reaching the core 912 and, thus, being absorbed. In the current potty training liner 900, unabsorbed fluid is acceptable as the unabsorbed fluid assists with the potty training of the child wearing the liner 900.

The interior section 942 may also include an acquisition distribution layer (ADL) 920 is positioned atop the SAF layer 916 and secured to the SAP layer 916 via an adhesive layer 922. For example, the ADL 920 may have hydrophilic properties that control the rate of liquid absorption by the core 912 and/or the SAP layer 916. ADL 920 may be hydrophilic in order to absorb a certain percentage of the fluid or may be hydrophobic with a high porosity in order to allow the fluid to pass through ADL 920 to core 912 or the SAP layer 916. In certain implementations, the ADL 920 may be a non-woven material with enhanced capillary action, thereby allowing fluids to distribute evenly thereon. In certain embodiments, ADL 920 may include materials that are optimized to retain a "wet feel," thereby enhancing the training benefits of potty training liner 900.

A top sheet 924 may be positioned atop the ADL 920 and secured via an adhesive layer 926. The top sheet 924 may be formed from a polyethylene nonwoven laminate. In some cases, the top sheet 924 may have hydrophilic properties and/or hydrophobic properties.

A left and right channel wall 928 and 930 may be affixed atop the top sheet 924. The channel wall 928 and 930 may be formed from a hydrophobic nonwoven secured via an adhesive 932 and 934 around an elastic layer 936 and 938. As discussed above, the channel wall 928 and 930 may form a channel 940 to secured the liquid associated with an insult against the skin of the wearer. Without the channel 940, an accident or insult may cause an overflow, when fluid hits the surface of the potty training liner 900 faster than the fluid can be absorbed.

In some cases, the channel walls 928 and 930 may be affixed to the or secured to the top sheet 924. In other examples, the channel walls 928 and 930 may be affixed to the or secured to the interior section 942. In one specific example, the channel walls 928 and 930 may be affixed to the or secured to the top sheet 924 may be formed from the material of the top sheet 924. The channel walls 928 and 930 may also maintain a predetermined distance from the center line (not shown) of the potty training liner 900. For example, each of the channel walls 928 and 930 may be less than 18 mm, less than 15 mm, less than 10 mm, or less than 8 mm from the center line. The channel walls 928 and 930 may also be greater than a predetermined distance from the outer edges of the potty training liner. For example, the channel walls 928 and 930 may be greater than 5.0 mm, greater than 10 mm, or greater than 15 mm from the edge of the potty training liner for the full length of the liner.

Figure 10:
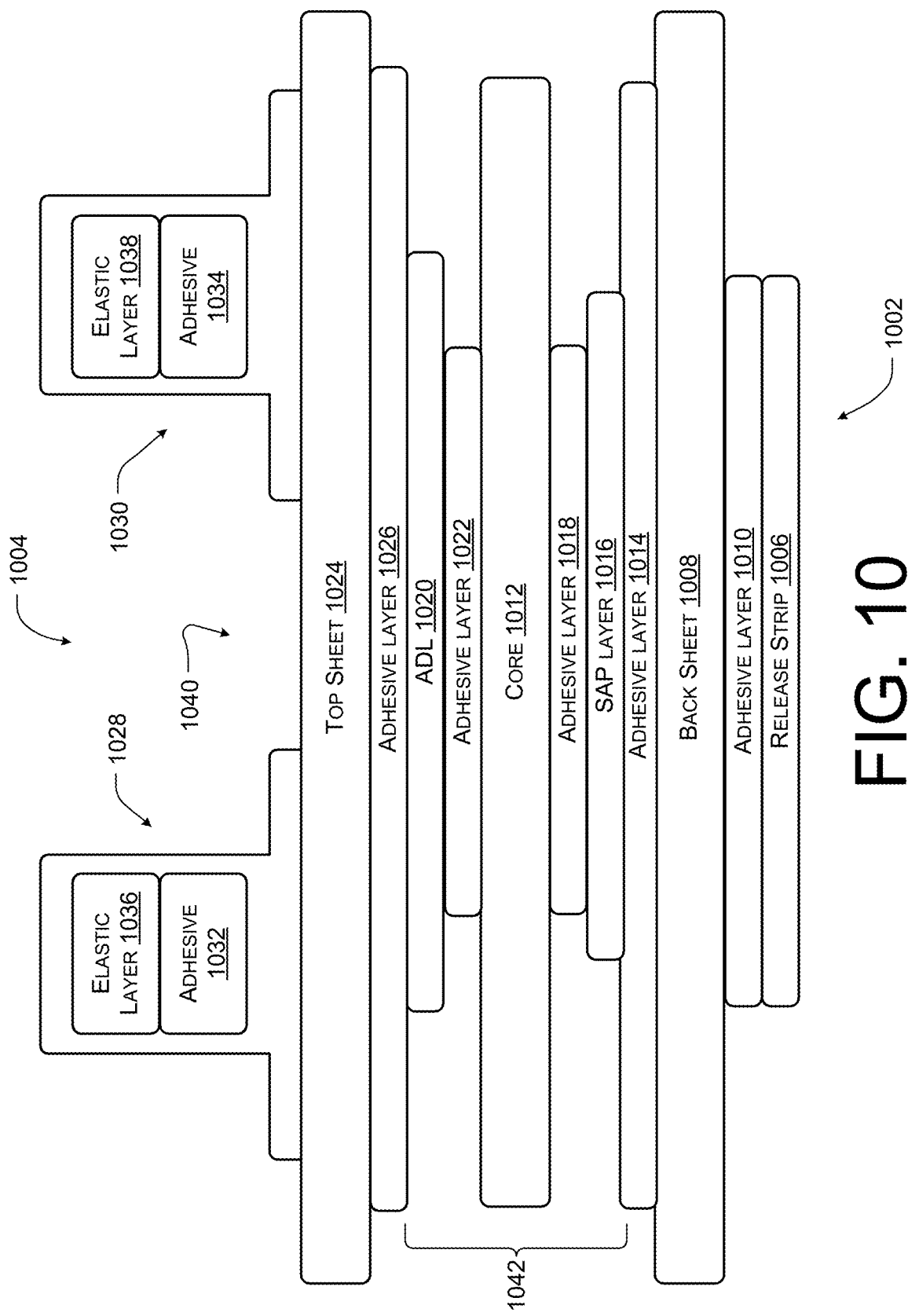
FIG. 10 illustrates another example cross sectional view of a potty training liner according to some implementations.

FIG. 10 illustrates another example cross sectional view of a potty training liner 1000 according to some implementations. As discussed above, in the current example, the area generally indicated by 1002 may be the bottom side of the potty training liner 1000 or the side exposed to the undergarment of the wearer. Likewise, the area, generally indicated by 1004, may be the top side of the potty training liner 1000 or the area in contact with the skin of the wearer. In some cases, the liner 1000 is machine-shaped into the configuration shown. The machine-shaping may include one or more adhesive applications including curing steps as well as one or more cutting steps to remove excess material.

In the current example, starting at the bottom 1002, a release strip 1006 may be releasably coupled to a back sheet 1008 via an achieves layer 1010. In this example, the release strip 1006 may be configured to be removed from the back sheet 1008 to expose the adhesive layer 1010, such that the adhesive layer 1010 may be used to secure the potty training liner 1000 to an undergarment (such as underwear).

The potty training liner 1000 may also have an interior section 1042 atop the back sheet 908. The interior section 942 may in turn be formed by multiple layers. For instance, in the current example, the interior section 942 may include a core 1012. The core 1012 may be less than 0.1 mm or less than 0.2 mm thick and formed from an airlaid SAF material or airlaid SAP material. In some cases, the core 912 may be formed from a fibrous matrix of cotton or wood pulp fluff which may be enhanced with a high-absorbency material or superabsorbent. In the current example, a SAP layer 1016 may be placed below the core 1012 as part of the interior section 1042 and atop the back sheet 1008. The SAP layer 916 may also be secured to the core 912 via an adhesive layer 1018 and the back sheet 1008 via an adhesive layer 1014.

The interior section 1042 may also include an ADL 1020 positioned atop the core 1012 and secured to the ore 1012 via an adhesive layer 1022. For example, the ADL 1020 may have hydrophilic properties that control the rate of liquid absorption by the core 1012 and/or the SAP layer 1016.

A top sheet 1024 may be positioned atop the ADL 1020 and secured via an adhesive layer 1026. The top sheet 1024 may be formed from a polyethylene nonwoven laminate. In some cases, the top sheet 1024 may have hydrophilic properties and/or hydrophobic properties.

A left and right channel wall 1028 and 1030 may be affixed atop the top sheet 1024. The channel wall 1028 and 1030 may be formed from a polyethylene nonwoven laminate secured via an adhesive 1032 and 1034 around an elastic layer 1036 and 1038. As discussed above, the channel wall 1028 and 1030 may form a channel 1040 to secured the liquid associated with an insult against the skin of the wearer. Without the channel 1040, an accident or insult may cause an overflow, when fluid hits the surface of the potty training liner 1000 faster than the fluid can be absorbed.

Figure 11:
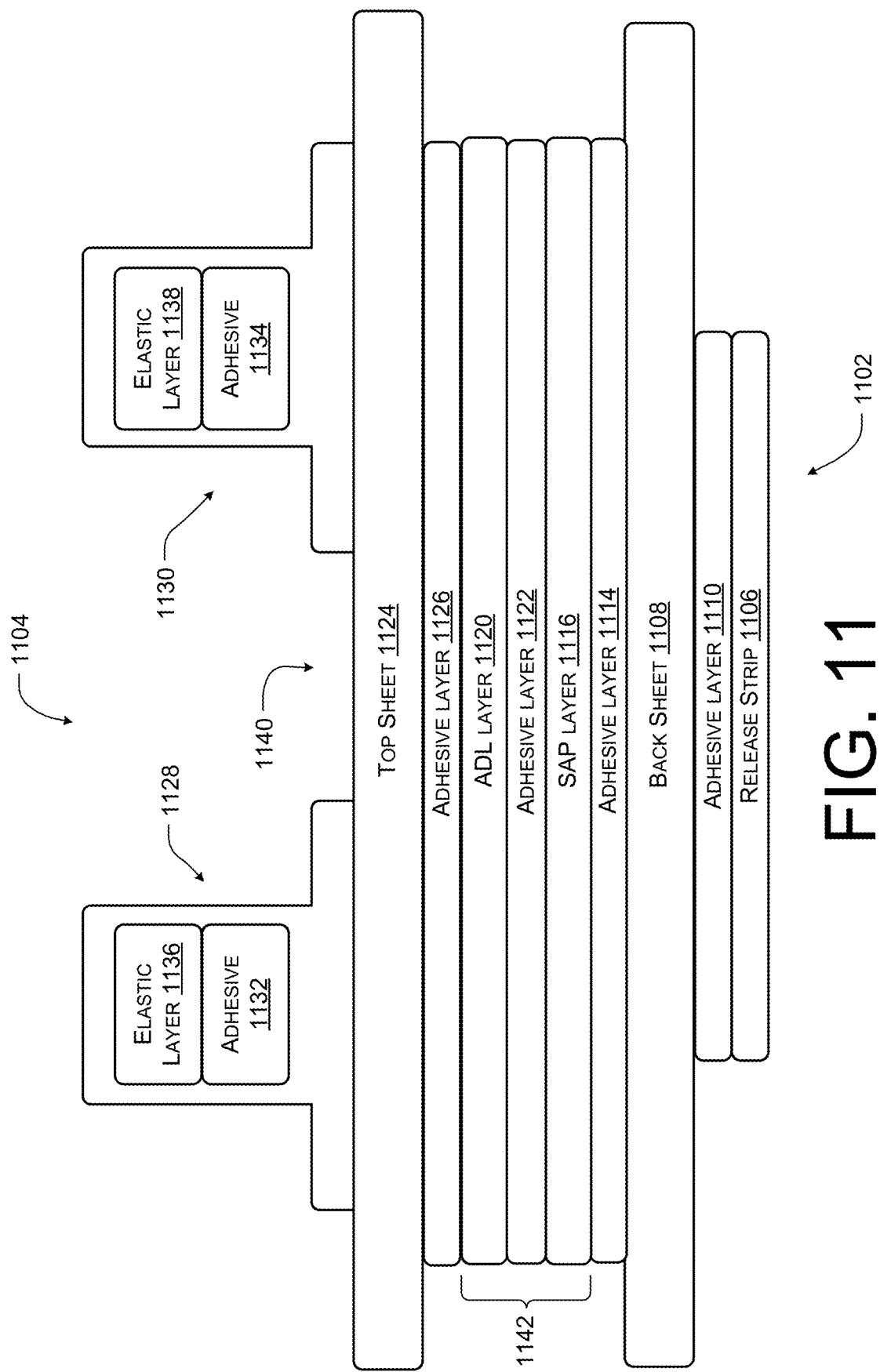
FIG. 11 illustrates another example cross sectional view of a potty training liner according to some implementations.

FIG. 11 illustrates another example cross sectional view of a potty training liner according to some implementations. Again, the area generally indicated by 1102 may be the bottom side of the potty training liner 1100 or the side exposed to the undergarment of the wearer. Likewise, the area, generally indicated by 1104, may be the top side of the potty training liner 1100 or the area in contact with the skin of the wearer. In some cases, the liner 1100 is machine-shaped into the configuration shown. The machine-shaping may include one or more adhesive applications including curing steps as well as one or more cutting steps to remove excess material.

In the current example, an interior section 1142 may include an ADL 1112 adhered to a SAP layer 1116 and exclude a core. Thus, in this implementation, unlike conventional potty training liners, diapers, and/or sanitary pads, the potty training liner 1100 may not include a core. By excluding the core layer, the potty training liner 1100 may be produced at a dry thickness of less than 1.0 mm, less than 2.0 mm, or less than 4.0 mm.

The potty training liner 1100 also includes a release strip 1106 releasably coupled to a back sheet 1108 via an achieves layer 1110. In this example, the release strip 1106 may be configured to be removed from the back sheet 1108 to expose the adhesive layer 1110, such that the adhesive layer 1110 may be used to secure the potty training liner 1100 to an undergarment (such as underwear).

The interior section 1142 may be positioned atop the back sheet 1108 and secured via an adhesive layer 1114. The interior section 1142 may also be positioned below a top sheet 1124 via an adhesive 1126. The top sheet 1124 may be formed from a polyethylene nonwoven laminate. In some cases, the top sheet 1124 may have hydrophilic properties and/or hydrophobic properties.

A left and right channel wall 1128 and 1130 may be affixed atop the top sheet 1124. The channel wall 1128 and 1130 may be formed from a polyethylene nonwoven laminate secured via an adhesive 1132 and 1134 around an elastic layer 1136 and 1138. As discussed above, the channel wall 928 and 930 may form a channel 1140 to secured the liquid associated with an insult against the skin of the wearer. Without the channel 1140, an accident or insult may cause an overflow, when fluid hits the surface of the potty training liner 1100 faster than the fluid can be absorbed.

FIG. 12 illustrates another example cross sectional view of a potty training liner 1200 according to some implementations. the area generally indicated by 1202 may be the bottom side of the potty training liner 1200. Likewise, the area, generally indicated by 1204, may be the top side of the potty training liner 1200.

In the current example, the potty training liner 1200 includes a back sheet 1208, an interior section 1242, and a top sheet 1224, as discussed above with respect to FIGS. 9-11. Each of the back sheet 1208, the interior section 1242, and the top sheet 1224 are secured to each other via adhesive layers 1214 and 1226 as shown. The potty training liner 1200 also includes a release strip 1206 releasably coupled to a back sheet 1208 via an achieves layer 1210, as discussed above.

The potty training liner 1200 may also include a left and right channel wall 1228 and 1230 may be affixed atop the top sheet 1224. In the illustrated example, the channel walls 1228 and 1230 may include stacked absorbent and superabsorbent material in a stair-step fashion extending outward from the channel 1240. In one example, the channel walls 1228 and 1230 may be formed in three layers, a bottom layer, a middle layer set off-center toward the outside, and a top layer set off-center toward the outside. The stair-step channel walls 1228 and 1230 create a low profile, with downwardly and inwardly collapsible walls, that minimizes blockage of fluid flow toward a center of the channel 1240 when compressed.

Each layer of the channel walls 1228 and 1230 may contain SAP which causes the walls 1228 and 1230 to swell, expanding laterally and horizontally to further trap fluid and to cause the fluid to move within the channel 1240. The movement may be felt by the user. In some cases, a fibrous absorbent material may be used in the wall s 1228 and 1230 may be formed from natural or synthetic fibers and by using methods such as air laying, spunbond, meltblown, or any of the methods known to those skilled in the art for making absorbent fibrous materials.

While FIGS. 1-12 are shown as different implementations, it should be understood that the features of FIGS. 1-12 may be applicable to any of the implementations illustrated. For example, the features of FIGS. 1-4 may be combined into a single implementation or embodiment. Further, colors can vary, and may include fun child-like designs, and/or a disappearing design via water activated ink, or positive reinforcement symbol on the inside top layer of the liner, as a positive indication that the liner is dry.

Although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

What is claimed is:

1. A potty training liner comprising:
   a back sheet;
   a top sheet positioned over the back sheet;
   a first channel wall extending upward from the top sheet, the first channel wall being greater than one inch in height;
   a second channel wall extending upward from the top sheet, the second channel wall being greater than one inch in height and positioned parallel to the first channel wall; and
   an interior section positioned between the back sheet and the top sheet, the interior section at least partially exposed by the top sheet at a location between the first channel wall and the second channel wall and configured to absorb 40 ml or less of fluid.

2. The potty training liner as recited in claim 1, wherein:
   the potty training liner has a front end and a back end, the back end opposite the front end, and a left side and a right side, the left side opposite the right side;
   the first channel wall is positioned greater than 6 mm from the right side of the potty training liner for a full length of the potty training liner; and
   the second channel wall is positioned greater than 6 mm from the left side of the potty training liner for the full length of the potty training liner.

3. The potty training liner as recited in claim 1, wherein:
   the potty training liner has a front end and a back end, the back end opposite the front end; and
   the first channel wall and the second channel wall maintain a height of greater than one and half inches for a full length of the potty training liner from the front end to the back end.

4. The potty training liner as recited in claim 1, wherein:
   the potty training liner has a front end and a back end, the back end opposite the front end; and
   the first channel wall and the second channel are in contact with the front end and the back end of the potty training liner.

5. The potty training liner as recited in claim 1, wherein:
   the potty training liner has a front end and a back end, the back end opposite the front end, and a left side and a right side, the left side opposite the right side;
   the first channel wall is positioned greater than 25 mm from the right side of the potty training liner for at least a portion of a length of the potty training liner; and
   the second channel wall is positioned greater than 25 mm from the left side of the potty training liner for at least a portion of a length of the potty training liner.

6. The potty training liner as recited in claim 1, wherein the first channel wall and the second channel wall are greater than or equal to two inches in height.

7. The potty training liner as recited in claim 1, wherein the potty training liner is configured to remain open around a leg of a user.

8. The potty training liner as recited in claim 1, wherein the potty training liner includes an adhesive on the back sheet, the adhesive to releasable secure the potty training liner to an undergarment during use, and wherein the undergarment supports the potty training liner during use.

9. The potty training liner as recited in claim 1, wherein a portion of the potty training liner comprising the top sheet, the back sheet, and the interior section is less than 5.0 mm thick when dry.

10. The potty training liner as recited in claim 1, wherein a portion of the potty training liner comprising the top sheet, the back sheet, and the interior section is less than 1.0 mm thick when dry.

11. A potty training liner comprising:
    a front end and a back end, the front end configured to rest in front of a user during use and the back end is configured to rest behind the user during use;
    a back sheet that is between 240 mm and 250 mm from the front end to the back end;
    a top sheet positioned over the back sheet, the top sheet being between 240 mm and 250 mm from the front end to the back end;
    a first channel wall extending upward from the top sheet, the first channel wall being greater than one inch in height and between 240 mm and 250 mm from the front end to the back end;
    a second channel wall extending upward from the top sheet, the second channel wall being greater than one inch in height, between 240 mm and 250 mm from the front end to the back end, and positioned parallel to the first channel wall;
    a channel formed between the first channel wall and the second channel wall, the channel being between 240 mm and 250 mm from the front end to the back end and between 45 mm and 50 mm wide;
    an interior section positioned between the back sheet and the top sheet, the interior section at least partially exposed by the top sheet at a location within the channel; and
    wherein a portion of the potty training liner comprising the top sheet, the back sheet, and the interior section is less than 1.0 mm thick when dry.

12. The potty training liner as recited in claim 11, wherein:
    the potty training liner has a front end and a back end, the back end opposite the front end, and a left side and a right side, the left side opposite the right side;
    the first channel wall is positioned greater than 10 mm from the right side of the potty training liner for a full length of the potty training liner; and
    the second channel wall is positioned greater than 10 mm from the left side of the potty training liner for the full length of the potty training liner.

13. The potty training liner as recited in claim 11, wherein the potty training liner is configured to remain open during a duration of use.

14. The potty training liner as recited in claim 11, wherein the interior section includes at least some hydrophobic areas and some hydrophilic areas to cause fluid to move within the channel after an accident.

15. The potty training liner as recited in claim 11, wherein the interior portion is configured to absorb 40 ml or less of fluid.

16. A potty training liner comprising:
- a front end and a back end, the front end configured to rest in front of a user during use and the back end is configured to rest behind the user during use;
- a back sheet;
- a top sheet;
- a first channel wall extending upward from the top sheet, the first channel wall being greater than one inch in height for the full length of the potty training liner from the front end to the back end;
- a second channel wall extending upward from the top sheet, the second channel wall being greater than one inch in height for the full length of the potty training liner from the front end to the back end and positioned parallel to the first channel wall, wherein the first channel wall and the second channel wall form a channel to allow liquid to pool and to move in response to a movement of the user; and
- an interior section positioned between the back sheet and the top sheet, the interior section at least partially exposed by the top sheet at a location between the first channel wall and the second channel wall and configured to absorb 40 ml or less of fluid.

17. The potty training liner as recited in claim 16, wherein the potty training liner maintains fluid in contact with skin of a user for greater than 20 minutes following an accident.

18. The potty training liner as recited in claim 16, wherein the first channel wall is greater than 1.5 inches for the full length of the potty training liner.

19. The potty training liner as recited in claim 16, wherein the first channel wall is greater than 2.5 inches for the full length of the potty training liner.

20. The potty training liner as recited in claim 16, wherein the first channel wall is positioned greater than 5.0 mm from a side edge of the potty training liner for the full length of the potty training liner.

\* \* \* \* \*